(12) United States Patent
Machold et al.

(10) Patent No.: US 10,799,354 B2
(45) Date of Patent: Oct. 13, 2020

(54) DEVICES, SYSTEMS, AND METHODS FOR RESHAPING A HEART VALVE ANNULUS

(71) Applicant: MVRx, Inc., San Mateo, CA (US)

(72) Inventors: Timothy R. Machold, Moss Beach, CA (US); David A. Rahdert, San Francisco, CA (US); Robert T. Chang, Belmont, CA (US); Ganesh Manoharan, Lisburn (GB)

(73) Assignee: MVRx, Inc., San Mateo, CA (US)

( * ) Notice: Subject to any disclaimer, the term of this patent is extended or adjusted under 35 U.S.C. 154(b) by 4 days.

(21) Appl. No.: 16/284,759

(22) Filed: Feb. 25, 2019

(65) Prior Publication Data

US 2019/0183645 A1   Jun. 20, 2019

Related U.S. Application Data

(62) Division of application No. 15/376,418, filed on Dec. 12, 2016, now Pat. No. 10,278,818.

(Continued)

(51) Int. Cl.
*A61F 2/24* (2006.01)
*A61B 17/04* (2006.01)
*A61B 17/00* (2006.01)

(52) U.S. Cl.
CPC ........ *A61F 2/2442* (2013.01); *A61B 17/0401* (2013.01); *A61B 2017/00243* (2013.01);
(Continued)

(58) Field of Classification Search
CPC ........ A61F 2/24; A61F 2/2412; A61F 2/2418; A61F 2/2448
(Continued)

(56) References Cited

U.S. PATENT DOCUMENTS

| | | | |
|---|---|---|---|
| 2,522,038 A | 9/1950 | Houghton |
| 3,143,742 A | 8/1964 | Cromie |

(Continued)

FOREIGN PATENT DOCUMENTS

| | | |
|---|---|---|
| CN | 103338726 | 10/2013 |
| CN | 104941016 | 9/2015 |

(Continued)

OTHER PUBLICATIONS

Alvarez et al., "Technical Improvements in the Repair of Acute Postinfarction Ventricular Septal Rupture", J Card Surg., vol. 7, No. 3, Sep. 1992, pp. 198-202.

(Continued)

*Primary Examiner* — Suzette J Gherbi
(74) *Attorney, Agent, or Firm* — DLA Piper LLP (US)

(57) ABSTRACT

Anchors for securing an implant within a body organ and/or reshaping a body organ are provided herein. Anchors are configured for deployment in a body lumen or vasculature of the patient that are curved or conformable to accommodate anatomy of the patient. Such anchors can include deformable or collapsible structures upon tensioning of a bridging element in a lateral direction, or segmented tubes that can be adjusted by tightening of one or more tethers extending therethrough. Such anchors can be used as a posterior anchor in a blood vessel in implant systems having a tensioned bridging element extending between the posterior anchor and an anterior anchor deployed at another location within or along the body organ. Methods of deploying such anchors, and use of multiple anchors or multiple bridging elements to a single anchor are also provided.

10 Claims, 11 Drawing Sheets

Related U.S. Application Data

(60) Provisional application No. 62/265,753, filed on Dec. 10, 2015.

(52) U.S. Cl.
CPC .............. *A61B 2017/00783* (2013.01); *A61B 2017/048* (2013.01); *A61B 2017/0417* (2013.01); *A61B 2017/0419* (2013.01); *A61B 2017/0464* (2013.01); *A61F 2/2487* (2013.01); *A61F 2220/0008* (2013.01)

(58) Field of Classification Search
USPC .................................................. 623/2.1–2.19
See application file for complete search history.

(56) References Cited

U.S. PATENT DOCUMENTS

| | | | |
|---|---|---|---|
| 3,686,740 A | 8/1972 | Shiley | |
| 4,016,884 A | 4/1977 | Kwan-Gett et al. | |
| 4,056,854 A | 11/1977 | Boretos et al. | |
| 4,275,469 A | 6/1981 | Gabbay | |
| 4,655,218 A | 4/1987 | Kulik et al. | |
| 4,788,966 A | 12/1988 | Yoon | |
| 4,850,354 A | 7/1989 | McGurk-Burleson et al. | |
| 4,865,600 A | 9/1989 | Carpentier et al. | |
| 4,889,118 A | 12/1989 | Schwiegerling | |
| 4,994,069 A | 2/1991 | Ritchart et al. | |
| 5,147,379 A | 9/1992 | Sabbaghian et al. | |
| 5,217,474 A | 6/1993 | Zacca et al. | |
| 5,236,450 A | 8/1993 | Scott | |
| 5,269,759 A | 12/1993 | Hernandez et al. | |
| 5,360,444 A | 11/1994 | Kusuhara | |
| 5,370,685 A | 12/1994 | Stevens | |
| 5,476,510 A | 12/1995 | Eberhardt et al. | |
| 5,492,538 A | 2/1996 | Johlin, Jr. | |
| 5,507,731 A | 4/1996 | Hernandez et al. | |
| 5,545,214 A | 8/1996 | Stevens | |
| 5,545,241 A | 8/1996 | Vanderauwera et al. | |
| 5,586,991 A | 12/1996 | Yoon | |
| 5,601,583 A | 2/1997 | Donahue et al. | |
| 5,624,430 A | 4/1997 | Eton et al. | |
| 5,669,918 A | 9/1997 | Balazs et al. | |
| 5,682,906 A | 11/1997 | Sterman et al. | |
| 5,695,515 A | 12/1997 | Orejola | |
| 5,697,382 A | 12/1997 | Love et al. | |
| 5,713,849 A | 2/1998 | Bosma et al. | |
| 5,716,370 A | 2/1998 | Williamson, IV et al. | |
| 5,716,397 A | 2/1998 | Myers | |
| 5,716,402 A | 2/1998 | Reif | |
| 5,741,287 A | 4/1998 | Alden et al. | |
| 5,759,185 A | 6/1998 | Grinberg | |
| 5,766,200 A | 6/1998 | Mazurek et al. | |
| 5,776,156 A | 7/1998 | Shikhman | |
| 5,776,189 A | 7/1998 | Khalid | |
| 5,779,721 A | 7/1998 | Nash | |
| 5,782,795 A | 7/1998 | Bays | |
| 5,792,155 A | 8/1998 | Van Cleef | |
| 5,814,097 A | 9/1998 | Sterman et al. | |
| 5,830,224 A | 11/1998 | Cohn et al. | |
| 5,851,185 A | 12/1998 | Berns | |
| 5,855,601 A | 1/1999 | Bessler et al. | |
| 5,895,404 A | 4/1999 | Ruiz | |
| 5,961,440 A | 10/1999 | Schweich, Jr. et al. | |
| 6,026,814 A | 2/2000 | Lafontaine et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,099,542 A | 8/2000 | Cohn et al. | |
| 6,102,932 A | 8/2000 | Kurz | |
| 6,162,168 A | 12/2000 | Schweich, Jr. et al. | |
| 6,165,119 A | 12/2000 | Schweich, Jr. et al. | |
| 6,183,411 B1 | 2/2001 | Mortier et al. | |
| 6,210,432 B1 | 4/2001 | Solem et al. | |
| 6,231,587 B1 | 5/2001 | Makower | |
| 6,260,552 B1 | 7/2001 | Mortier et al. | |
| 6,261,222 B1 | 7/2001 | Schweich, Jr. et al. | |
| 6,287,339 B1 | 9/2001 | Vazquez et al. | |
| 6,299,637 B1 | 10/2001 | Shaolian et al. | |
| 6,312,464 B1 | 11/2001 | Navia | |
| 6,312,465 B1 | 11/2001 | Griffin et al. | |
| 6,332,864 B1 | 12/2001 | Schweich, Jr. et al. | |
| 6,332,893 B1 | 12/2001 | Mortier et al. | |
| 6,338,470 B1 | 1/2002 | Steely et al. | |
| 6,338,735 B1 | 1/2002 | Stevens | |
| 6,338,740 B1 | 1/2002 | Carpentier | |
| 6,352,543 B1 | 3/2002 | Cole | |
| 6,385,472 B1 | 5/2002 | Hall et al. | |
| 6,402,781 B1 | 6/2002 | Langberg et al. | |
| 6,419,695 B1 | 7/2002 | Gabbay | |
| 6,419,696 B1 | 7/2002 | Ortiz et al. | |
| 6,440,164 B1 | 8/2002 | Dimatteo et al. | |
| 6,454,799 B1 | 9/2002 | Schreck | |
| 6,458,153 B1 | 10/2002 | Bailey et al. | |
| 6,475,230 B1 | 11/2002 | Bonutti et al. | |
| 6,503,272 B2 | 1/2003 | Duerig et al. | |
| 6,514,194 B2 | 2/2003 | Schweich, Jr. et al. | |
| 6,537,198 B1 | 3/2003 | Vidlund et al. | |
| 6,589,160 B2 | 7/2003 | Schweich, Jr. et al. | |
| 6,616,684 B1 | 9/2003 | Vidlund et al. | |
| 6,626,899 B2 | 9/2003 | Houser et al. | |
| 6,629,534 B1 | 10/2003 | St. Goar et al. | |
| 6,652,540 B1 | 11/2003 | Cole et al. | |
| 6,656,221 B2 | 12/2003 | Taylor et al. | |
| 6,669,679 B1 | 12/2003 | Savage et al. | |
| 6,669,709 B1 | 12/2003 | Cohn et al. | |
| 6,676,699 B2 | 1/2004 | Shiu | |
| 6,685,739 B2 | 2/2004 | Dimatteo et al. | |
| 6,702,826 B2 | 3/2004 | Liddicoat et al. | |
| 6,709,456 B2 | 3/2004 | Langberg et al. | |
| 6,723,038 B1 | 4/2004 | Schroeder et al. | |
| 6,764,510 B2 | 7/2004 | Vidlund et al. | |
| 6,793,618 B2 | 9/2004 | Schweich, Jr. et al. | |
| 6,805,711 B2 | 10/2004 | Quijano et al. | |
| 6,893,459 B1 | 5/2005 | Macoviak | |
| 6,913,608 B2 | 7/2005 | Liddicoat et al. | |
| 6,945,978 B1 | 9/2005 | Hyde | |
| 7,004,176 B2 | 2/2006 | Lau | |
| 7,070,618 B2 | 7/2006 | Streeter | |
| 7,077,862 B2 | 7/2006 | Vidlund et al. | |
| 7,166,126 B2 | 1/2007 | Spence et al. | |
| 7,166,127 B2 * | 1/2007 | Spence ................. | A61F 2/2445 623/2.37 |
| 7,316,706 B2 * | 1/2008 | Bloom .................. | A61F 2/2487 606/151 |
| 7,691,144 B2 | 4/2010 | Chang et al. | |
| 7,695,510 B2 * | 4/2010 | Bloom .................. | A61F 2/2454 623/2.36 |
| 7,901,454 B2 * | 3/2011 | Kapadia ........... | A61B 17/00234 623/2.1 |
| 7,967,808 B2 | 6/2011 | Fitzgerald et al. | |
| 8,100,820 B2 * | 1/2012 | Hauser .................. | A61F 2/2451 600/37 |
| 8,187,207 B2 | 5/2012 | Machold et al. | |
| 8,262,725 B2 * | 9/2012 | Subramanian ........ | A61F 2/2454 623/2.36 |
| 8,506,624 B2 | 8/2013 | Vidlund et al. | |
| 8,690,858 B2 | 4/2014 | Machold et al. | |
| 8,956,407 B2 * | 2/2015 | Macoviak ............. | A61F 2/2442 623/2.37 |
| 8,968,395 B2 | 3/2015 | Hauser et al. | |
| 8,979,922 B2 | 3/2015 | Jayasinghe et al. | |
| 8,979,925 B2 | 3/2015 | Chang et al. | |
| 9,168,043 B2 | 10/2015 | Van der Burg et al. | |
| 9,498,331 B2 | 11/2016 | Chang et al. | |
| 9,861,475 B2 * | 1/2018 | Machold .............. | A61F 2/2418 |
| 10,201,423 B2 * | 2/2019 | Chang .................. | A61F 2/2442 |
| 10,219,902 B2 * | 3/2019 | Machold .............. | A61F 2/2445 |
| 10,278,818 B2 * | 5/2019 | Machold .............. | A61F 2/2442 |
| 2001/0010017 A1 | 7/2001 | Letac et al. | |
| 2001/0021872 A1 | 9/2001 | Bailey et al. | |
| 2001/0051824 A1 | 12/2001 | Hopkins et al. | |
| 2002/0010481 A1 | 1/2002 | Jayaraman | |

(56) References Cited

U.S. PATENT DOCUMENTS

| | | |
|---|---|---|
| 2002/0032481 A1 | 3/2002 | Gabbay |
| 2002/0065554 A1 | 5/2002 | Streeter |
| 2002/0094573 A1 | 7/2002 | Bell |
| 2002/0123802 A1 | 9/2002 | Snyders |
| 2002/0129820 A1 | 9/2002 | Ryan et al. |
| 2002/0138138 A1 | 9/2002 | Yang |
| 2002/0183841 A1 | 12/2002 | Cohn et al. |
| 2003/0014104 A1 | 1/2003 | Cribier |
| 2003/0040792 A1 | 2/2003 | Gabbay |
| 2003/0069593 A1 | 4/2003 | Tremulis et al. |
| 2003/0078465 A1 | 4/2003 | Pai et al. |
| 2003/0120340 A1 | 6/2003 | Liska et al. |
| 2003/0130731 A1* | 7/2003 | Vidlund ............... A61F 2/2454 623/2.37 |
| 2003/0139819 A1 | 7/2003 | Beer et al. |
| 2003/0181928 A1 | 9/2003 | Vidlund et al. |
| 2003/0191528 A1 | 10/2003 | Quijano et al. |
| 2003/0199974 A1 | 10/2003 | Lee et al. |
| 2003/0212453 A1* | 11/2003 | Mathis ................. A61F 2/2466 623/2.11 |
| 2003/0233022 A1 | 12/2003 | Vidlund et al. |
| 2004/0059333 A1 | 3/2004 | Carl et al. |
| 2004/0059415 A1 | 3/2004 | Schmieding |
| 2004/0127982 A1 | 7/2004 | Machold et al. |
| 2004/0148019 A1 | 7/2004 | Vidlund et al. |
| 2004/0162610 A1 | 8/2004 | Liska et al. |
| 2004/0210304 A1 | 10/2004 | Seguin et al. |
| 2004/0243230 A1 | 12/2004 | Navia et al. |
| 2004/0260317 A1* | 12/2004 | Bloom ................. A61F 2/2487 606/151 |
| 2005/0010277 A1 | 1/2005 | Chuter |
| 2005/0055089 A1 | 3/2005 | Macoviak et al. |
| 2005/0075723 A1 | 4/2005 | Schroeder et al. |
| 2005/0197694 A1 | 9/2005 | Pai et al. |
| 2005/0222488 A1 | 10/2005 | Chang et al. |
| 2005/0228422 A1 | 10/2005 | Machold et al. |
| 2005/0267571 A1 | 12/2005 | Spence et al. |
| 2006/0009800 A1 | 1/2006 | Christianson et al. |
| 2006/0074484 A1 | 4/2006 | Huber et al. |
| 2006/0195012 A1 | 8/2006 | Mortier et al. |
| 2006/0241745 A1 | 10/2006 | Solem |
| 2006/0282161 A1 | 12/2006 | Huynh et al. |
| 2007/0043391 A1 | 2/2007 | Moszner et al. |
| 2007/0083259 A1* | 4/2007 | Bloom ................. A61F 2/2454 623/2.11 |
| 2007/0203391 A1 | 8/2007 | Bloom et al. |
| 2007/0244553 A1* | 10/2007 | Rafiee ................. A61F 2/2451 623/2.11 |
| 2007/0282430 A1 | 12/2007 | Thommen et al. |
| 2008/0091264 A1 | 4/2008 | Machold et al. |
| 2009/0043381 A1 | 2/2009 | Macoviak et al. |
| 2009/0069885 A1* | 3/2009 | Rahdert ............. A61B 17/0469 623/2.1 |
| 2010/0130992 A1 | 5/2010 | Machold et al. |
| 2010/0161044 A1 | 6/2010 | Chang et al. |
| 2012/0035718 A1 | 2/2012 | Chang et al. |
| 2012/0123532 A1* | 5/2012 | Mathis ................. A61F 2/2451 623/2.37 |
| 2012/0209377 A1 | 8/2012 | Machold et al. |
| 2012/0232645 A1 | 9/2012 | Machold et al. |
| 2014/0222138 A1 | 8/2014 | Machold et al. |
| 2015/0057705 A1 | 2/2015 | Vidlund |
| 2015/0112433 A1* | 4/2015 | Schweich, Jr. ....... A61F 2/2409 623/2.38 |
| 2015/0173901 A1* | 6/2015 | Nieminen ............. A61F 2/2451 623/2.36 |
| 2015/0182337 A1* | 7/2015 | Chang ................. A61F 2/2451 623/2.1 |
| 2016/0067043 A1 | 3/2016 | Machold et al. |
| 2016/0374810 A1* | 12/2016 | Mathis ................. A61F 2/2451 623/2.37 |

FOREIGN PATENT DOCUMENTS

| | | |
|---|---|---|
| WO | 03028558 | 4/2003 |
| WO | 03055417 | 7/2003 |
| WO | 2004045463 | 6/2004 |
| WO | 2006041877 | 4/2006 |

OTHER PUBLICATIONS

Antunes, "Submitralleft Ventricular Aneurysms Correction by a New Transatrial Approach", J Thorac Cardiovasc Surg., vol. 94, No. 2, Aug. 1987, pp. 241-245.

Bailey et al., "Surgical Repair of Mitral Insufficiency", Diseases of the Chest, vol. 19, No. 2, Feb. 1951, pp. 125-137.

Bailey et al., "The Surgical Correction of Mitral Insufficiency by the Use of Pericardial Grafts", The Journal of Thoracic Surgery, vol. 28, No. 6, Dec. 1954, pp. 551-603.

Barnard et al., "A Surgical Approach to Mitral Insufficiency", The British Journal of Surgery, vol. 48, May 1961, pp. 655-662.

Bolling et al., "Early Outcome of Mitral Valve Reconstruction in Patients with End-Stage Cardiomyopathy", J Thorac Cardiovasc Surgical, vol. 109, 1995, pp. 676-683.

Bolling et al., "Intermediate-Term Outcome of Mitral Reconstruction in Cardiomyopathy", Journal of Thoracic Cardiovascular Surgery, vol. 115, No. 2, Feb. 1998, pp. 381-388.

Cicek et al., "Left Ventricular Endoaneurysmorrhaphy: Effect on Left Ventricular Size, Shape and Function", Cardiology, vol. 88, No. 4, Jul.-Aug. 1997, pp. 340-345.

Cooley, "Repair of Postinfarction Ventricular Septal Defect", J Card Surg., vol. 9, No. 4, Jul. 1994, pp. 427-429.

Cox, "Surgical Management of Left Ventricular Aneurysms: A Clarification of the Similarities and Differences Between . . . ", Semin Thorac Cardiovasc Surg., vol. 9, No. 2, Apr. 1997, pp. 131-138.

Daggett et al., "Surgery for Post-Myocardial Infarct Ventricular Septal Defect", Ann Surg., vol. 186, No. 3, Sep. 1977, pp. 260-271.

Daggett, "Surgical Technique for Early Repair of Posterior Ventricular Septal Rupture", J Thorac Cardiovasc Surg., vol. 84, No. 2, Aug. 1982, pp. 306-312.

Davila et al., "A Method for the Surgical Correction of Mitral insufficiency", Surgery, Gynecology and Obstetrics, vol. 98, No. 4, Apr. 1954, pp. 407-412.

Davila et al., "Circumferential Suture of the Mitral Ring: A Method for the Surgical Correction of Mitral Insufficiency", Journ of Thoracic Surg, vol. 30, No. 5, Nov. 1955, pp. 531-563.

Davila et al., "The Clinical and Physiological Criteria for Surgical Correction of Mitral Insufficiency", Journal of Thoracic Surg, vol. 35, No. 2, Feb. 1958, pp. 206-231.

De Silva et al., "Postinfarction Ventricular Septal Defect An Efficacious Technique for Early Surgical Repair", J Thorac Cardiovasc Surg., vol. 97, No. 1, Jan. 1989, pp. 86-89.

Dor, "Left Ventricular Aneurysms: the Endoventrciular Circular Patch Plasty", Semin Thorac Cardiovasc Surg., vol. 9, No. 2, Apr. 1997, pp. 123-130.

Edmunds et al., "Septal Defect", Atlas of Cardiothoracic Surgery, 1990, 4 pages.

Fucci et al., "Improved Results with Mitral Valve Repair Using New Surgical Techniques", European Journal of Cardio-Thoracic Surgery, vol. 9, Issue 11, Nov. 1, 1995, pp. 621-626.

Glover et al., "The Treatment of Mitral Insufficiency by the Purse-String Technique", Journal of Thoracic Surgery, vol. 33, No. 1, Jan. 1957, pp. 75-101.

Harken et al., "The Surgical Correction of Mitral Insufficiency", Surgical Forum, vol. 4, 1953, pp. 4-7.

Harken et al., "The Surgical Correction of Mitral Insufficiency", The Journal of Thoracic Surgery, vol. 28, No. 6, 1954, pp. 604-627.

Harlan et al., "Manual of Cardiac Surgery", vol. 2, Figs. 16.3-16.4, 1981, 3 pages.

Henderson et al., "The Surgical Treatment of Mitral Insufficiency; Experimental Use of Transplanted Pericardium in Dogs", Surgery, vol. 33, Issue No. 6, 1953, pp. 858-868.

(56) References Cited

OTHER PUBLICATIONS

Jatene, "Left Ventricular Aneurysmectomy. Resection or Reconstruction", J Thorac Cardiovasc Surgical, vol. 89, No. 3, Mar. 1985, pp. 321-331.
Kameda et al., "Annuloplasty for Severe Mitral Regurgitation Due to Dilated Cardiomyopathy", Ann Thorac Surg., vol. 61, No. 6, Jun. 1996, pp. 1829-1832.
Kay et al., "Surgical Treatment of Mitral insufficiency", Surgery, vol. 37, No. 5, May 1955, pp. 697-706.
Koniaris et al., "Dynamic Retention: A Technique for Closure of the Complex Abdomen in Critically Iii Patients", Archives of Surgery, vol. 136, No. 12, Dec. 2001, pp. 1359-1362.
Kuykendall et al., "Surgical Correction of Chronic Mitral Insufficiency in Dogs", Surgery, vol. 44, No. 4, Oct. 1958, pp. 718-725.
Liedtke et al., "Functional Reductions in Left Ventricular Volume", Thorac Cardiovasc Surg., vol. 71, No. 2, Feb. 1976, pp. 195-206.
McKenzie et al., "Current Concepts in Surgical Correction of Acquired Mitral Insufficiency", Circulation, Clinical Progress, vol. 28, Oct. 1963, pp. 603-616.
Moore et al., "Unsuitability of Transventricular Autogenous Slings for Diminishing Valvular Insufficiency", From the Department of Surgery, vol. 33, No. 2, Feb. 1953, pp. 173-182.
Murray et al., "Reconstruction of the Valves of the Heart", The Canadian Medical Association Journal, vol. 38, No. 4, Apr. 1938, pp. 317-319.
Rankin et al., "A Clinical Comparison of Mitral Valve Repair Versus Valve Replacement in Ischemic Mitral Regurgitation", J Thorne Cardiovasc Surg., vol. 95, No. 2, Feb. 1988, pp. 165-177.
Saab et al., "Left Ventricular Aneurysm: A New Surgical Approach", Thorac Cardiovasc Surg., vol. 37, No. 1, Feb. 1989, pp. 11-19.
Sakakibara, "A Surgical Approach to the Correction of Mitral Insufficiency", Annals of Surgery, vol. 142, No. 2, Aug. 1954, pp. 196-203.
Salati et al., "Severe Diastolic Dysfunction after Endoventriculoplasty.", J Thorac Cardiovasc Surg., vol. 109, No. 4, Apr. 1995, pp. 694-701.
Skillington et al., "Surgical Treatment for Infarct-Related Ventricular Septal Defects", J Thorac Cardiovasc Surg., vol. 99, No. 5, May 1990, pp. 798-808.
Sosa et al., "Recurrent Ventricular Tachycardia Associated With Postinfarction Aneurysm. Results of Left Ventricular", J Thorac Cardiovasc Surg., vol. 103, No. 5, May 1992, pp. 855-860.
Tashiro et al., "Extended Endocardial Repair of Postinfarction Ventricular Septal Rupture: New Operative Technique-Modification", J Card Surg., vol. 9, No. 2, Mar. 1994, pp. 97-102.
Templeton et al., "Experimental Reconstruction of Cardiac Valves by Venous and Pericardial Grafts", Annals of Surgery vol. 129, No. 2, Feb. 1949, pp. 161-176.
Wilson, "Studies in Experimental Mitral Obstruction in Relation to the Surgical Treatment of Mitral Stenosis", The British, Journal of Surgery, vol. 18, No. 70, Oct. 1930, pp. 259-274.
Yacoub et al., "Anatomic Correction of the Syndrome of Prolapsing Right Coronary Aortic Cusp, Dilatation of the Sinus . . . ", J Thorac Cardiovasc Surg., vol. 113, No. 2, Feb. 1997, pp. 253-260.

* cited by examiner

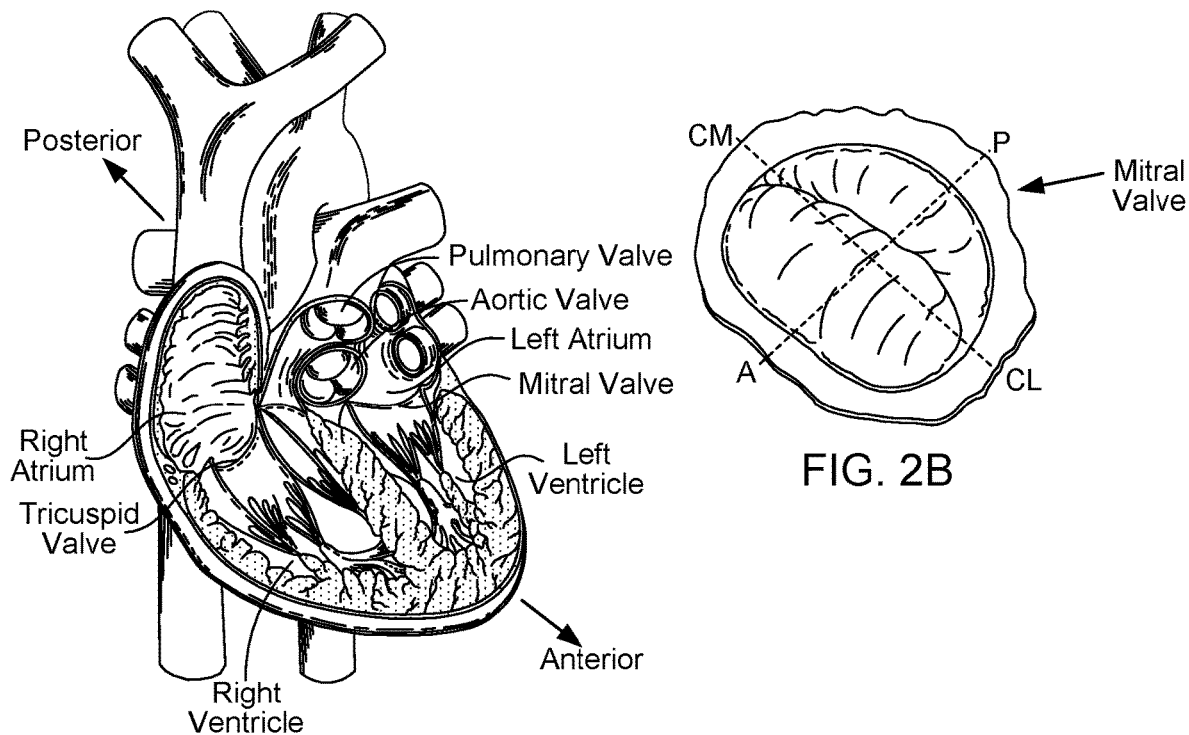
FIG. 2A
FIG. 2B
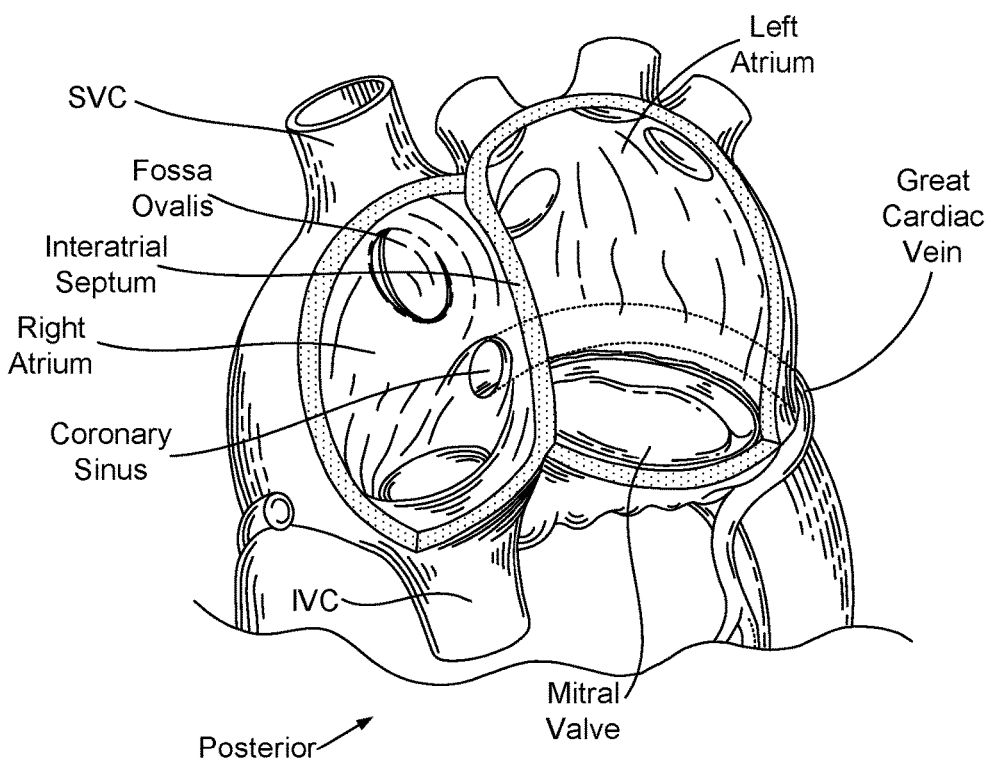
FIG. 2C

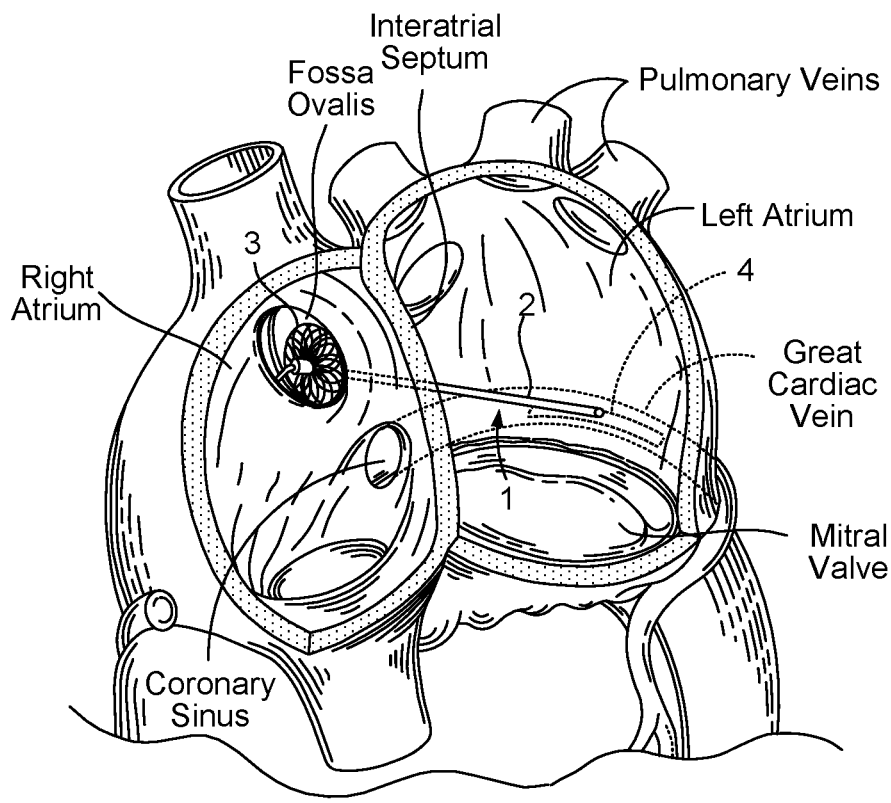
FIG. 3
(Prior Art)
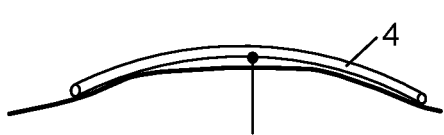
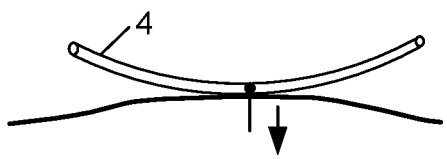
FIG. 4A			FIG. 4B

DEVICES, SYSTEMS, AND METHODS FOR RESHAPING A HEART VALVE ANNULUS

CROSS-REFERENCES TO RELATED APPLICATIONS

The present application is a Divisional of U.S. patent application Ser. No. 15/376,418 filed Dec. 12, 2016 (Allowed); which claims the benefit and priority of U.S. Provisional Appln. No. 62/265,753 filed Dec. 10, 2015, the contents of which are herein incorporated by reference in their entirety for all purposes.

FIELD OF THE INVENTION

The invention relates to devices, systems, and methods for anchoring of an implant within the body and/or reshaping an organ within the body. In particular, the invention may be directed to improving the function of a heart valve by reshaping a mitral valve annulus with an anchored implant system for treatment of mitral valve regurgitation. The invention provides improved posterior anchoring devices for use in implant systems employing an anterior anchor attached to a bridging element that spans the left atrium and attaches to a posterior anchor located in the great cardiac vein.

BACKGROUND OF THE INVENTION

The healthy human heart (is a muscular two-side self-regulating pump slightly larger than a clenched fist, as can be seen in FIGS. 2A-2C. It is composed of four chambers; right atrium (RA) and right ventricle (RV) and the left atrium (LA) and LV (LV). The RA collects poorly oxygenated blood returning from the lower body via the inferior vena cava (IVC) and from the head and upper body via the superior vena cava (SVC) and delivers it through the tricuspid valve to the RV. The RV then contracts which has the effect of closing the tricuspid valve and forcing the blood through the pulmonary valve into the pulmonary artery for circulation to the lungs. The left side of the heart collects the oxygenated blood in the LA returning from the lungs via the pulmonary veins. From, there the blood is delivered to the LV. The LV then powerfully contracts having the effect of closing the mitral valve (MV) and forcing the blood through the aortic valve into the aorta and thence throughout the body.

The interatrial septum, a wall composed of fibrous and muscular parts that separates the RA and LA, as can be seen in FIG. 2C. The fibrous interatrial septum is, compared to the more friable muscle tissue of the heart, a more materially strong tissue structure in its own extent in the heart. An anatomic landmark on the interatrial septum is an oval, thumbprint sized depression called the oval fossa, or fossa ovalis, as can be seen in FIG. 2C, which is a remnant of the oval foramen and its valve in the fetus. It is free of any vital structures such as valve structure, blood vessels and conduction pathways. Together with its inherent fibrous structure and surrounding fibrous ridge, which makes it identifiable by angiographic techniques, the fossa ovalis is the favored site for trans-septal diagnostic and therapeutic procedures from the right into the left heart. Before birth, oxygenated blood from the placenta was directed through the oval foramen into the LA, and after birth the oval foramen closes. The heart's four valves function primarily to ensure the blood does not flow in the wrong direction during the cardiac cycle i.e. backflow from the ventricles to the atria or backflow from the arteries into the corresponding ventricles.

The synchronous pumping actions of the left and right sides of the heart constitute the cardiac cycle. The cycle begins with a period of ventricular relaxation, called ventricular diastole. At the beginning of ventricular diastole (i.e. ventricular filling), the aortic and pulmonary valves are closed to prevent backflow from the arteries into the ventricles. Shortly thereafter, the tricuspid and mitral valves open to allow flow from the atria into the corresponding ventricles. Shortly after ventricular systole (i.e. ventricular contraction and emptying) begins, the tricuspid and mitral valves close to prevent backflow from the ventricles into the corresponding atria. The aortic and pulmonary valves then open to permit discharge of blood into the arteries from the corresponding ventricles. The opening and closing of the heart valves occur primarily as a result of pressure differences. For example, the opening and closing of the mitral valve occurs as a result of the pressure differences between the LA and the LV. During ventricular diastole, when the LV is relaxed, the blood returning from the lungs into the LA causes the pressure in the atrium to exceed that in the LV. As a result, the mitral valve opens, allowing blood to flow from the LA into the LV. Subsequently as the now full ventricle contracts in ventricle systole, the intraventricular pressure rises above the pressure in the atrium and pushes the mitral valve shut.

The mitral and tricuspid valves are defined by fibrous rings of collagen, each called an annulus, which forms a part of the fibrous skeleton of the heart. The annulus provides attachment to cusps or leaflets of the mitral valve (called the anterior and posterior cusps or leaflets) and the three cusps or leaflets of the tricuspid valve. The cusps of a healthy mitral valve are shown in FIG. 2B. Proper closing function is also aided by a tethering action of chordae tendineae and one or more papillary muscles. Also of structural relevance to this invention and located in the vicinity of the annulus of the mitral valve is the coronary sinus and its tributaries including the great cardiac vein (GVC), as can be seen in FIG. 2C. The GVC generally courses around the lower wall of the LA outside the atrial chamber but within the atrial wall. The GVC empties into the RA through the coronary sinus.

Each of the valves in question is a one-way valve that function to allow blood to flow only in the appropriate direction. If any of the valves does not function properly, that will affect the efficiency of the heart and may result in significant health issues. For example, failure of the mitral valve between the LA and the LV, to fully seal while the LV is contracting results in some portion of the blood in the LV being expelled retrograde back into the LA. This is generally termed mitral regurgitation and depending on severity, can result in insufficient blood flow throughout the body with resultant serious health implications.

II. Characteristics and Causes of Mitral Valve Dysfunction

When the LV contracts after filling with blood from the LA, the walls of the ventricle move inward and release some of the tension from the papillary muscle and chords. The blood pushed up against the under-surface of the mitral leaflets causes them to rise toward the annulus plane of the mitral valve. As they progress toward the annulus, the leading edges of the anterior and posterior leaflet come together forming a seal and closing the valve. In the healthy heart, leaflet coaption occurs near the plane of the mitral annulus. The blood continues to be pressurized in the LV until it is ejected into the aorta. Contraction of the papillary muscles is simultaneous with the contraction of the ventricle and serves to keep healthy valve leaflets tightly shut at peak contraction pressures exerted by the ventricle.

In a healthy heart, the dimensions of the mitral valve annulus create an anatomic shape and tension such that the leaflets coapt, forming a tight junction, at peak contraction pressures. Where the leaflets coapt at the opposing medial and lateral sides of the annulus are called the leaflet commissures CM, CL, as shown FIG. 2B. Valve malfunction can result from the chordae tendineae (the chords) becoming stretched, and in some cases tearing. When a chord tears, this results in a leaflet that flails. Also, a normally structured valve may not function properly because of an enlargement of or shape change in the valve annulus. This condition is referred to as a dilation of the annulus and generally results from heart muscle failure. In addition, the valve may be defective at birth or because of an acquired disease. Regardless of the cause, mitral valve dysfunction can occur when the leaflets do not coapt at peak contraction pressures. When this occurs, the coaption line of the two leaflets is not tight at ventricular systole. As a result, an undesired back flow of blood from the LV into the LA can occur.

This mitral regurgitation, if significant in amount, may have has several serious health consequences. For example, blood flowing back into the atrium may cause high atrial pressure and reduce the flow of blood into the LA from the lungs. As blood backs up into the pulmonary system, fluid leaks into the lungs and causes pulmonary edema. Another health problem resulting from mitral valve dysfunction is the reduction of ejection fraction of the heart, or the effective pumping of the blood through the body of that blood that does enter the LV. The blood volume regurgitating back into the atrium reduces the volume of blood going forward into the aorta causing low cardiac output. Excess blood in the atrium as a result of mitral valve regurgitation may also over-fill the ventricle during each cardiac cycle and causes volume overload in the LV. Over time, this may result in dilation of the LV and indeed the entire left side of the heart. This may further reduce the effective cardiac output and further worsen the mitral regurgitation problem by dilating the mitral valve annulus. Thus, once the problem of mitral valve regurgitation begins, the resultant cycle may cause heart failure to be hastened. Treating the problem therefore not only has the immediate effect of alleviating the heart output problems mentioned above, but also may interrupt the downward cycle toward heart failure.

III. Current Treatment Methods

Various methods of treating this serious heart condition have been suggested. In one approach, the native valve is removed and replaced with a new valve, such as described in U.S. Pat. No. 6,200,341 to Jones et al and U.S. Pat. No. 7,645,568 to Stone. While this approach may be of use in some situations, such surgical procedures generally require open chest surgery, which is invasive and often contraindicated for very sick or old patients, which includes many of those suffering from mitral valve regurgitation.

Another method which has been suggested is to apply tension across the LV to reshape the LV, thereby affect the functioning of the mitral valve, such as described in U.S. 2005/0075723 to Schroeder et al. This approach uses a splint that spans across a ventricle and extends between epicardial pads that engage outside surfaces of the heart. This approach is also invasive and potentially problematic as it penetrates an outer surface of the heart.

Another method that has been suggested is the attempted constriction of the LA by means of a belt like constricting device extending inside the GVC which runs along the posterior wall of the LA, such as described in U.S. 2002/0183841 A1 to Cohn et al. While this may be partially helpful, often the device fails to sufficiently alter the shape of the left atrium to fully resolve the failure of the leaflets to coapt.

Yet another method that has proven particularly useful is to employ a system that applies direct tension across the width of the LA and across the minor axis of the annulus of the mitral valve, such as shown in FIG. 3. System 1 utilizes a bridging element 2 that extends between an anterior anchor 3 and a posterior anchor 4. The anterior anchor 3 is generally located at the wall between the LA and the RA, for example, on the fossa ovalis on the septal wall, and is attached to the bridging element 2 that spans the LA. Posterior anchor 4 is located across the atrium posterior to the anterior anchor and may be located outside the atrium chamber in the GVC. The bridging element is affixed to the posterior anchor and provides a bridge across the LA between the septum. The GVC and is tensioned to directly affect the shape of the LA, and in particular, the annulus of the mitral valve. By adjusting the tension of the bringing element, the shape of the LA and particularly the annulus of the mitral valve can be adjusted to achieve optimum closure of the mitral valve during cardiac function. An example of this approach is described in detail in U.S. Pat. No. 8,979,925 B2 to Chang et al., the entire contents of which are incorporated herein by reference for all purposes.

This approach has many advantages over conventional approaches, including avoiding invasive procedures such as open heart surgery or being placed on a heart-lung machine. However, there are still a number of challenges that must be addressed. While the anterior anchor provides relatively robust and secure anchoring with the fossa ovalis, anchoring within a body vessel, such as the GCV is more problematic. While the fossa ovalis is defined by a notable depression, which lends itself to having an anchor disposed within, the GCV lacks any notable anatomical features and is defined by a relatively smooth-walled vessel along the outer wall of the left atrium. In addition, the heart is a highly dynamic organ such that any implant disposed therein is subjected to highly variable forces and movements due to the contortions of the heart muscle during a pumping cycle of the heart. These aspects make anchoring within the GCV particularly challenging. Thus, there is need for devices, systems and methods that allow for robust and dependable anchoring within a vessel, such as the GCV. There is further need for such anchoring devices that can withstand considerable forces over the lifetime of the device. There is further need for such anchoring devices that can assist in reshaping of an organ, such as the heart.

BRIEF SUMMARY

The present invention is a directed towards anchors for deployment in a body lumen or vessel that provide improved anchoring against laterally applied loads. Such anchors can be used to secure implants within a body organ or to reshape a body organ by engaging a portion of an organ wall with the anchor. Of particular use, are implant devices and systems for improving heart function, primarily for improving mitral valve function by reshaping the LA. In any of the embodiments described herein, the implant and anchors are configured to be delivered and deployed intravascularly.

Such anchor devices and systems can be particularly effective in reshaping the mitral valve annulus by engaging a posterior portion of the left atrium. In such an approach, an exterior force is provided external the GVC and is generally perpendicular to the GVC. In a mitral valve treatment implant system, the tension applied by the bridging element to the posterior anchor. It is therefore beneficial to have devices and methods that spread the anchoring force as broadly and evenly as possible to avoid injury to the GVC wall and to move the atrial wall more effectively. In one aspect, the invention pertains to a posterior anchor that is designed to spread tensioning forces for example, along the interior wall of the GVC and to prevent the posterior anchor from sliding longitudinally in the GVC. Sliding of the anchor could cause the bridging element to slice or tear the GVC wall where it passes through the GVC wall. The present invention also is directed towards methods for spreading tensioning forces along the GVC and preventing longitudinal motion of the posterior anchor within the GVC. In particularly, such methods include delivery and deployment of a posterior anchor for use in a mitral valve treatment system that applies the exterior force broadly along the GVC to more effectively move the wall of the left atrium inwardly.

In one aspect, the invention provides an anchor for securing an implant within a body organ and reshaping of a body organ of a patient. The anchor can include a substantially cylindrical body that is sized and dimensioned for delivery and deployment in a body lumen or blood vessel of the patient. In some embodiments, the anchor is configured to be deployed in a surgically formed sac or opening. The cylindrical body is configured to be deformable or collapsible in a lateral direction. The cylindrical body includes a substantially rigid backbone extending longitudinally being disposed on or within the cylindrical body. The backbone includes an attachment region along an intermediate portion thereof for coupling with a bridging element of the implant. The cylindrical body is configured such that when the bridging element is coupled to the attachment region and tensioned while the anchor is disposed within the body lumen or blood vessel, the backbone deforms or collapses the cylindrical body so as to conform along one side of an inner wall of the body lumen or blood vessel. Typically, the cylindrical body is configured to engage 180 degrees or less of an inner wall of the body lumen or blood vessel when laterally deformed or collapsed. The anchor can be sized and dimensioned for intravascular delivery and deployment within a blood vessel of the patient.

The backbone can be longitudinally curved so as to conform to anatomy of the patient. In some embodiments, the cylindrical body is formed of a plastically compressible foam material so as to increase a contact surface of the cylindrical body against the wall of the blood vessel while maintaining patency of the blood vessel when deployed.

In some embodiments, the cylindrical body is an expandable scaffold. Typically, such scaffolds include an expanded configuration in which the scaffold circumferentially engages the blood vessel and a laterally collapsed configuration in which scaffold collapses to conform to an anatomy of the patient, for example, a C-shape so as to engage at least a portion of one side of the blood vessel when the bridging element is tensioned. Typically, the scaffold has a radially compressed configuration to facilitate intravascular delivery through the blood vessel. In some embodiments, the expandable scaffold comprises folding zones extending longitudinally on opposite sides of the scaffold and offset from the backbone so as to facilitate lateral collapse when a lateral force is applied to the backbone. It is appreciated, that the anchor could be configured to conform in a similar manner to various other shapes for use in other lumens or body structures. Such scaffolds can be formed of a metal, various polymers, or any combination of suitable materials. Some scaffolds are formed of a mesh or web material to facilitate ingrowth of adjacent tissue. In some embodiments, the scaffolds can include barbs or other features to inhibit sliding along the lumen when anchored.

In another aspect, implant systems are provided herein. Such implant systems can include an tensionable bridge element that extends between an anterior anchor for positioning within or against a body organ or structure and a posterior anchor for deployment within a body lumen or vessel adjacent the organ or structure. In some embodiments, the implant system is for treating a human heart valve. In some embodiments, the implant system includes: an anterior anchor configured to positioned within a desired location along or within an organ of the patient; a bridging element, and a posterior anchor. The cylindrical body is sized and dimensioned for delivery and deployment in a blood vessel of the body organ, typically the GCV. The cylindrical body being deformable or collapsible in a lateral direction and has a substantially rigid backbone disposed on or within the cylindrical body that is attached to the bridging element. The bridging element is adapted to span a chamber of the heart between an anterior anchor and a posterior anchor and maintain sufficient tension so as to provide a desired spacing between the anterior anchor and posterior anchor thereby reshaping the chamber of the heart so as to improve function of the heart valve.

In another aspect, anchors for deployment within a body lumen or vessel that include anti-flipping features are provided. Such anchors can include: an elongate main body being curved or conformable so as to accommodate an anatomy of the patient and an anti-flipping feature adapted to resist flipping or inversion of the elongate main body when a bridging element attached to the main body is tensioned along a direction of curvature of the elongate main body. Typically, the elongate main body is hollow or has a lumen extending therethrough to facilitate delivery and deployment via a guidewire or catheter.

In some embodiments, the anchor includes a substantially rigid elongate support member with an attachment region on an intermediate portion thereof for coupling with the bridging element and the anti-flipping features may include a jacket or cover fit over the rigid support. The jacket can be shaped and formed of a flexible material. In some embodiments, the jacket extending beyond each opposite end of the elongate support member to provide atraumatic tips. The anti-flipping feature can be formed in various shapes to further improve engagement within the body lumen or vessel and inhibit flipping. In some embodiments, the jacket is shaped to include a planar portion on one side for engagement of a wall of the vessel or body lumen. The planar portion can be curved or contoured along one or more axes, for example the planar portion can be curved in a widthwise direction to accommodate a curvature of the vessel wall and can be curved along a lengthwise direction to accommodate a curved path of the vessel. In some embodiments, the jacket is shaped to includes a planar central portion that is wider than each opposing end portion of the jacket. This planar portion provides an increased contact area for engagement with the lumen, which further inhibits flipping. The central portion can include an attachment region to allow attachment of the bridging element. In some embodiments, the attachment region includes an opening within the planar central portion to allow passage of a bridging element to a rigid support member disposed within the jacket. It is appreciated, however, that the bridging elements can be attached by any suitable means.

In other embodiments, the anti-flipping feature includes a movable link attached to the main body and coupling the bridging element to the main body. The link is typically short, substantially shorter than the length of the main body and is hollow such that the bridging element can pass therethrough. In some embodiments, the link is pivotally coupled to an intermediate portion of the main body and is pivotally movable along a plane of curvature of the elongate so as to be foldable against the elongate main body during delivery and laterally extended from the main body when deployed.

In other embodiments, the anti-flipping feature is a design of the anchor that includes a main body defined by a plurality of segments and one or more tethers extending through an interior of the elongate main body that are engaged with opposite end portions of the elongate main body such that tensioning of the one or more tethers in a lateral direction draws the plurality of segments together thereby curving the main body in the direction along which the one or more tethers are tensioned. In some embodiments the main body is a single hollow tube segmented by a plurality of kerfs distributed along a length of the single tube. In some embodiments, the anchor includes first and second tethers coupled with opposite ends of the hollow tube, respectively, and exiting through one or more openings in a center portion of the hollow tube such that the tube assumes a curved shape when the tubular ends of the tube are forced inward by tensioning of the first and second tethers. In other embodiments, the anchor includes a single tether extending directly from one end of the tube and secured to the other end of the tube by a fastener, the tether shortened to a length at which the hollow tube assumes a desired radius of curvature for deployment. In still other embodiments, the anchor includes a tether that extends through an interior of the hollow tube and exits from opposite end portions of the hollow tube for attachment to another anchor, either directly or through a bridging member or element, such that tensioning of the tether draws the opposite end portions together thereby curving the hollow tube. In another embodiment, the anchor is defined by a hollow tube comprises a plurality of independent segments having interfacing ends that are angled to facilitate curvature of the hollow tube when the one or more tethers are tensioned.

In another aspect, methods of anchoring an implant and reshaping a body organ of a patient are provided herein. Such methods can includes steps of: delivering and deploying an anterior anchor within a desired location along or within an organ of a patient; delivering a posterior anchor within a vasculature of the patient adjacent the body organ, the posterior anchor being conformable to an anatomy of the patient upon deployment of the posterior anchor; delivering a first bridging element that extends between the anterior anchor and the posterior anchor so as to attach the anterior anchor with the posterior anchor when deployed; and conforming the posterior anchor to a desired shape to accommodate the anatomy of the patient by tensioning the first bridging element while interfaced with the posterior anchor and the anterior anchor, wherein tensioning the first bridging element comprises shortening the first bridging element to maintain a desired spacing between the anterior anchor and the posterior anchor so as to reshape the body organ by engagement of the conformed posterior anchor.

In some embodiments, the anchoring methods includes use of a posterior anchor having a cylindrical body that is laterally deformable or collapsible and has a substantially rigid backbone attached to the cylindrical body. In some such methods, conforming the posterior anchor includes tensioning the first bridging element while attached to the rigid backbone so as to deform or collapse the cylindrical body with the rigid backbone shortening against the anatomy of the patient. In some embodiments, where the cylindrical body is scaffold, conforming the anchor includes laterally collapsing the scaffold by folding the scaffold along the folding zones while tensioning the bridging element attached to the backbone. Some such methods further includes: delivering the scaffold in a radially compressed configuration via a guidewire or catheter; and radially expanding the scaffold within the vasculature before laterally collapsing the scaffold.

In some embodiments, the anchoring methods include use of an anchor defined as a segmented tube. In such methods, conforming the anchor can include shortening of one or more tether interfaced with opposite end portions of the segmented tube. For example, where the posterior anchor includes a segmented tube and a first tether attached to a first end of the segmented tube and exits the segmented tube along a central portion thereof, shortening the first tether thereby curving a portion of the segmented tube between the first end and the central portion. In some embodiments, such methods further include shortening a second tether extending from a second opposite side of the segmented tube and exiting the segmented tube along the central portion thereof thereby curving another portion of the segmented tube between the second end and the central portion.

In some embodiments utilizing anchors defined by segmented tubes, the bridging element including multiple bridging elements or tethers, each directly between an end of the segmented tube and the anterior anchor such that shortening both bridging elements or tethers elements under tension curves the segmented tube so as to conform to anatomy against which the posterior anchor is engaged. In some embodiments, the bridging element extends across a chamber of an organ and penetrates a tissue against which the anchor is engaged. In some embodiments, the anchor can include a single tether extending through the segmented tube and attached at both ends to the anterior anchor so as to form a loop, such that shortening or tightening of the loop draws opposite ends of the segment tube inward so as to curve the posterior anchor.

BRIEF DESCRIPTION OF THE DRAWINGS

FIG. 2A is an anatomic superior view of a section of the human heart showing the tricuspid valve in the right atrium, the mitral valve in the LA, and the aortic valve in between, with the tricuspid and mitral valves open and the aortic and pulmonary valves closed during ventricular diastole (ventricular filling) of the cardiac cycle.

FIG. 2B illustrates a healthy mitral valve demonstrating full coaptation between leaflets along the entire major axis of the valve.

FIG. 2C is an anatomic anterior perspective view of the left and right atriums, with portions broken away and in section to show the interior of the heart chambers and associated structures, such as the fossa ovalis, coronary sinus, and the GVC.

FIG. 3 shows a conventional implant system having a bridge spanning the left atrium between an anterior anchor disposed in the fossa ovalis and a curved posterior anchor disposed in the GCV.

FIGS. 4A-4B illustrate the tendency of a conventional curved posterior anchor to flip or invert when tension forces are applied.

DETAILED DESCRIPTION

Figure 1A:
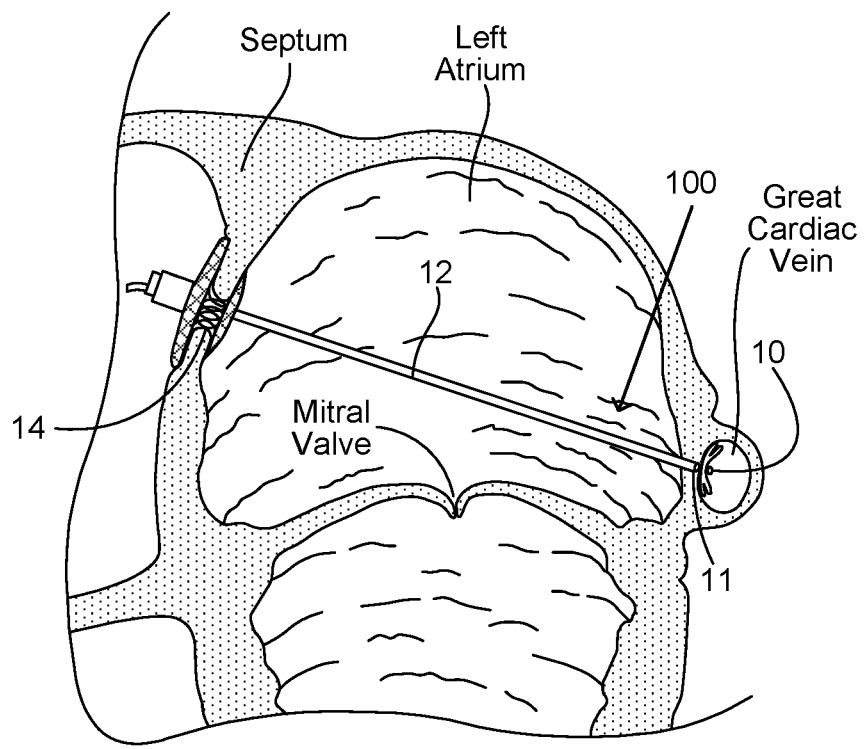
FIGS. 1A and 1B illustrate a heart implant system that includes an inter-atrial bridging element that spans the mitral valve annulus between an anterior anchor disposed in the fossa ovalis and a posterior anchor positioned in the GVC in accordance with aspects of the invention.

The present invention relates to devices, systems, and methods for intravascular anchoring of an implant within the body and/or reshaping an organ within the body by use of an anchor deployed within a body lumen or body vessel. Implants described herein and associated anchors are directed to improving the function of a heart valve by reshaping a mitral valve annulus for treatment of mitral valve regurgitation. It is appreciated that any heart implant system can utilize a posterior anchor having any of the features described herein, or any combination thereof. Further, although the following embodiments describe posterior anchors for use in heart implant systems having a bridging element that spans the left atrium between an anterior anchor and the posterior anchor disposed in the GCV, it is appreciated that the features described herein pertain to implant systems for treatment of any heart valve, or can pertain to any anchor for deployment in a body lumen and could be utilized in various other implant systems at other bodily locations in accordance with the concepts described herein.

One important feature of the heart valve treatment systems for treatment of mitral valve regurgitation presented herein is the posterior anchor. As shown in the implant system 100 in FIGS. 1A-1B, once installed, the posterior anchor 10 is generally located within the GVC. It is important for the posterior anchor to spread tensioning forces from the bridging element as broadly as possible along the length of the GVC to avoid tearing the GVC/LA wall or pulling the posterior anchor through the tissue of the GVC/LA wall and thus reducing or eliminating the tension on the bridging element. It is also helpful to the treatment of restoring the shape and anatomical distance of the LA from the septum and the annulus of the mitral valve that the tensioning on the bridging element pull much of the LV wall in the area of the annulus forward toward the septum. If the tension is instead concentrated at a point on the LA wall, this may tend to pull just a limited point area forward and not significantly move the entire wall of the LA. The tissue may pucker or fold inward rather than pull the full wall of the LA forward.

Unlike previous GCV device concepts where the device is placed solely within the GCV to reshape the left atrium, these systems rely on additional lateral force applied to the LA wall that is supplied by, attached to and maintained by an anchor on the substantially thicker and robust septal wall to a preferred septal-lateral spacing that is controlled by the operator. Although GCV only devices attempt to reshape the path of the GCV inward, their ability to move surrounding tissue, including portions of the ventricle, is severely limited all applied forces must resolve or balance in the GCV itself. There is a need for an anchor for the GCV that distributes these substantially large forces in a manner that uniformly moves the lateral wall to cause the leaflets to co-apt without trauma or erosion, ideally maintaining as much of the natural shape, contour, and function of the GCV and the septal-lateral spacing with the septum as possible.

Among the challenges associated with such implant systems is the difficulty in providing stable, secure engagement of the posterior anchor along the posterior wall of the left atrium while disposed within the GCV. First, since the inside wall of the GCV along the left atrium is generally smooth-walled without any notable anatomical features, the posterior anchor has a tendency to slide or move, which can lead to variability of the septal-lateral spacing provided by the implant system such that some level of mitral valve regurgitation may still occur. Furthermore, since the heart is subjected to a significant amount of cyclical movement during the cardiac cycle, this sliding movement of the posterior anchor over time can lead to erosion of tissues or enlargement of the penetration through which the bridging element extends, leading to tearing of the LA wall along the GCV. Secondly, in such systems having curved or flexible posterior anchors, the curvature of the anchor often does not match the natural curvature of the atrium wall such that the posterior anchor fails to consistently engage a large enough portion of the posterior wall of the left atrium to ensure a desired reshaping of the annulus is maintained throughout the entire cardiac cycle. Also, since the posterior anchor is typically tensioned by a bridging element attached along a mid-portion to distribute anchoring forces, tensioning of a curved posterior anchor tends to flip a rigid curved anchor or invert a semi-rigid curved anchor during the cardiac cycle, as shown in FIGS. 4A-4B, which further frustrates the purpose of the posterior anchor.

To address these challenges, presented herein are anchors having improved design features that provide increased stability and consistency in anchoring as well as improved engagement with adjacent tissues, particularly when deployed in a body vessel. In one aspect, the anchor has an elongate main body sized and dimensioned for delivery and deployment within the vasculature of the patient. For heart implant systems, such anchors can have a length dimension between 1 cm and 10 cm, typically between 2 cm and 8 cm, so as to distribute laterally applied anchoring forces and engage a substantial portion of the heart wall. The anchor can have a width dimension of between 0.5 cm and 5 cm, typically between 1 cm and 3 cm. The anchor can be contoured or curved along its length dimension, as well as along a width dimension, so as to conform more closely to an anatomy of the body lumen or an adjacent organ. In some embodiments, the anchor is specially shaped so as to engage at least a portion of one side of the vessel in which it is deployed, while leaving the remainder of the vessel open to facilitate blood flow therethrough. Examples of such shapes includes a D or C-shape, as well as an ovoid shape, all of which increase the contact area of the posterior anchor along the one side of the body vessel, while maintaining patency of the vessel.

Figure 1B:
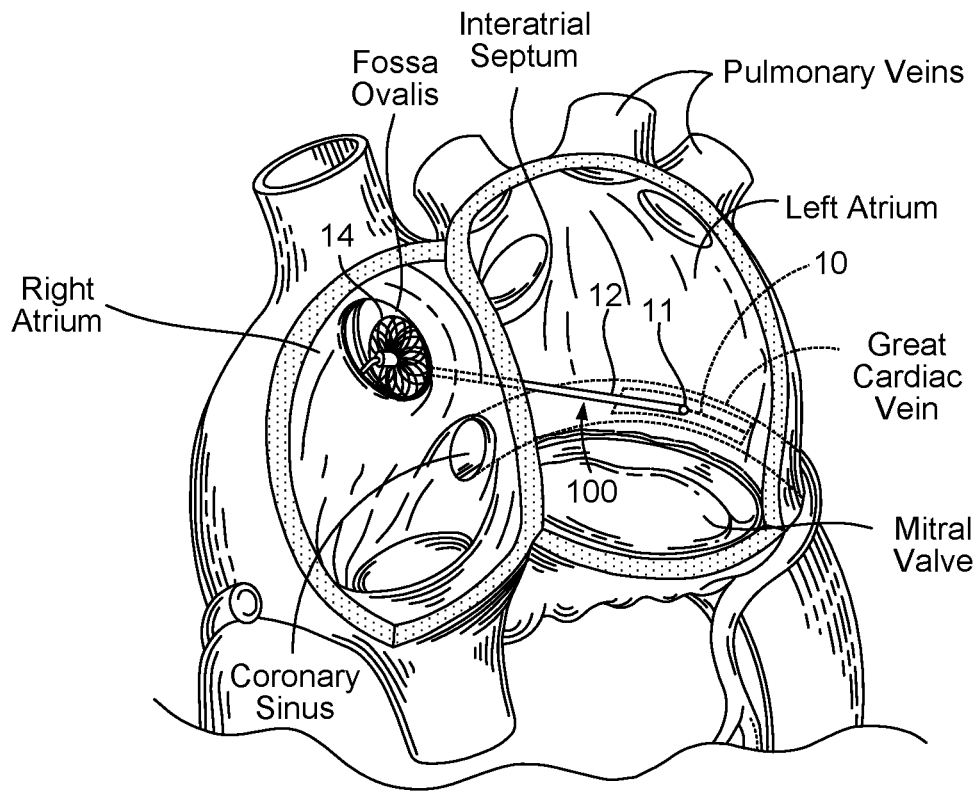

FIGS. 1A and 1B illustrate an example heart valve treatment system 100 that includes bridging element 12 that spans across the left atrium, extending between anterior anchor 14 secured in the fossa ovalis and posterior anchor 10 deployed in the GCV. In this embodiment, posterior anchor 10 is a cylindrical structure, such as those detailed in FIG. 13A, that is laterally collapsible so as to provide an increased contact surface area along the inner wall of the GCV along the wall of the LA when deployed. As can be seen in FIG. 1B, posterior anchor 10 is also curved along its length so as to conform more closely with the anatomy of the outside curvature of the LA along which the GCV extends. Posterior anchor 10 can further include an anti-flipping feature 11 to inhibit flipping or inversion along its length due to movement and forces caused imparted by the structures of the heart during the cardiac cycle. While a particular design of posterior anchor is shown in FIGS. 1A-1B, it is appreciated that system 100 could utilize any suitable posterior anchor, including any of those described herein or any suitable anchor features in accordance with the concepts described herein.

In some embodiments, the intravascular anchors are defined as an elongate member having a central rigid portion along where the tensioning member attaches and flexible outer ends. The central rigid portion can include a stress-relief feature such as an attachment point that is flexible, movable or pivots to accommodate abrupt movements of the tensioning member so as to maintain engagement of the anchor with adjacent tissues during the heart cycle. The flexible outer ends can be provided by a modifications to the central rigid portion (e.g. notches, kerfs), or can be provided by additional components, such as a polymer jacket or cover that fits over the rigid portion.

In some embodiments, the intravascular anchor is contoured or shaped to conform to at least a portion of one side of the vessel in which it is disposed. In some embodiments, the intravascular anchor has a fixed shape, while in other embodiments, the shape of the anchor is flexible or conformable. In some embodiments, the intravascular anchor can assume multiple configurations of varying size and shape to facilitate delivery and deployment. In any of the embodiments described herein, the anchor can be defined with a hollow lumen therethrough to facilitate intravascular delivery via a guidewire or catheter.

These and other aspects of the improved anchor can be further understood by referring to the embodiments depicted in FIGS. 5-13B. While these embodiments describe a posterior anchor for use in a tensioned heart implant, it is appreciated that these anchor features can apply to various other types of anchors for implants in various other bodily locations. For example any of the features described can be used in an implant to provide improved anchoring, which can include improved conformance against anchored tissues, improved distribution of forces, and improved engagement of tissues to facilitate reshaping of a body organ.

Figure 5:
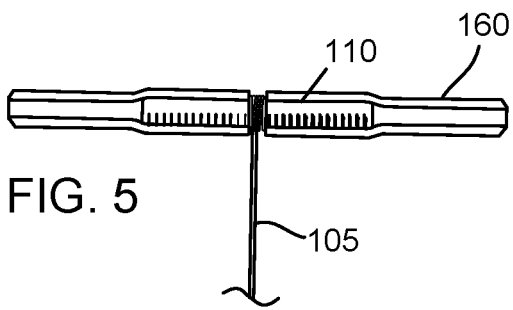
FIG. 5 illustrates a posterior anchor with a jacket attached to a tensioning member in accordance with some embodiments.

FIG. 5 illustrates a posterior anchor defined as a T-bar 110 that is jacketed to provide strain relief and an atraumatic tip configuration. In some embodiments, a thin or thick walled polymeric jacket 160 can be fit over a conventional rigid T-bar anchor to provide an atraumatic surface. T-bar 110 is coupled with the bridge element 105, which can be a suture, tether, or any element suitable for spanning across the left atrium and maintaining tension sufficient to reshape the atrium. The jacket 160 is sized and dimensioned so that the end portions of the jacket extend beyond the ends of the rigid T-bar 110. Jacket 160 can be formed of PTFE, high silicone soft-block urethanes, silicones, or any suitable material and can further include a thin fabric outer covering, such as polyester. In some embodiments, the jacket is preferably formed of a material that encourages tissue ingrowth. The jacket may be held in place by adhesive or shrunk over the T-bar or both. In this embodiment, jacket 160 is defined as two end pieces abutting the inner attached central bridge attachment, although the jacket could be defined a single piece jacket attached over an entire length of the T-bar, such as in the next embodiment described below. The tip extensions may be shaped to reduce tissue strain, for example curved or serpentine (not shown) to increase stability and aid delivery. This approach allows a conventional T-bar anchor to be retrofit so as to change a size and/or shape of the anchor, provide improved or variable flexibility along its length or provide various other advantageous characteristics.

Figure 6:
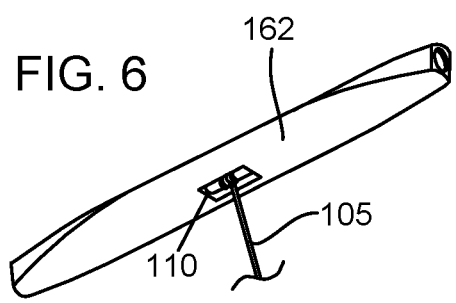
FIG. 6 illustrates a posterior anchor with a jacket attached to a tensioning member, in accordance with some embodiments.

FIG. 6 illustrates another posterior anchor configured as a rigid T-bar backbone 110 covered by a shaped jacket 162. Shaped jacket 162 can be polymeric semi-rigid or compliant "surfboard" that fits over the rigid T-bar 110. Such a configuration is advantageous as it allows a conventional rigid T-bar anchor to be retrofit to assume any shape, contour or flexibility desired for a particular application. In this embodiment, which is configured for use in the heart implant system described above, the shaped jacket 162 is shaped to be planar or flattened on one side so as to increase tissue contact area with the interior wall of the GVC toward the LA and to further distribute anchoring contact forces. The planar portion can be flat or curved to accommodate the shape of the vessel. In this embodiment, the planar portion is included on a center portion having increased width than either end portion and includes an opening near a center of the planar center portion, which facilitates engagement of the planar center portion with the wall of the vessel. This increased width dimension and planar portion provide improved resistance to flipping. Shaped jacket 162 can be formed thin along its posterior/anterior dimension so that it lies relatively flat against the GCV wall, thus maximizing blood flow in the GCV. This configuration also served to stabilize posterior anchor and resist flipping. As with other embodiments, surfaces may be coated or constructed of material that induces tissue ingrowth. Shaped jacket can be formed of various polymeric materials, including PTFE, high silicone soft-block urethanes, silicones, other implant grade elastomers. An optional thin fabric may be employed, such as polyester covering the polymeric jacket, to promote tissue growth or inhibit sliding. The size of the device can vary, of course depending on the desire of the surgeon and the particular requirements of the patient, for example a large male vs. a pediatric patient, but one advantageous size for typical adult patients would be, for example, 12F round or oval shaped T-bar. Such a link could be combined as a "backbone" to stabilize and strengthen other jacketed or wire form structures discussed above. The wire form may be metal, plastic, or any other material that will allow the rigid backbone to collapse the form as described above.

Although a straight version of shaped jacket 162 is shown in FIG. 6, it is appreciated that shaped jacket 162 could be formed with a predetermined curved shape along its length to match the curvature of the mitral annulus or the GCV or both. Having a width close to that of the GCV, gaining more purchase of the lateral wall, the tendency of the curve to flip or right would be thwarted. In some embodiments, a delivery catheter used to deliver the anchor can include mounting features that allow axial rotation to allow proper placement of the anchor aligning the curvature with the GCV. Such feature can include lumens or guides that or any interfacing feature to allow manipulation of an orientation of the anchor during deployment. Shaped jacket can be constructed from a semi-rigid material to allow tracking over a guidewire with quasi straightening of its shape and more significant bending upon removal of the guidewire and release of the device. One or more radio-opaque features can be added to the anchor to allow a clinician to visualize its position and orientation during delivery and deployment. While in these embodiments, bridge element 105 is depicted as a suture that is wound about a mid-portion of the T-bar 110, it is appreciated that various other bridging elements and suitable means of attachment (e.g. adhesive, welding, couplings) could be used.

While some conventional systems have utilized curved posterior anchors, such anchors have a tendency to flip (when of a rigid construction) or invert (when of a more flexible construction). This action can be further understood by referring to the conventional heart valve treatment system 1 shown in FIG. 3, which includes a bridging element 2 extending from an anterior anchor 3 to a mid-point of a conventional posterior anchor 4, defined as rigid curved tubular member. When a thin curved posterior anchor, especially a rigid curved anchor, is placed in the GVC, and tension is applied to the internal curvature of the arc, especially near the apex, the forces will have a tendency to flip the curved anchor in the GVC and present the exterior edge of the curvature to the passage between the GVC and the atrium.

FIGS. 4A-4B illustrates this flipping tendency. Flipping the anchor reaches a more stable energy condition, and therefore this is the configuration the anchor will tend to seek. In considering this flip in configuration, it is important to remember that the distal anchor, in place in the GVC, is far from a still curved structure lying against static curved vein. It is in place in a vessel full of flowing blood imbedded in the wall of a heart that is beating generally as many as 75 times or so a minute. As the posterior anchor is tossed about and buffeted by flowing blood, the anchor will quickly seek the most stable orientation in relation to the tension forces from the bridging element, and flip into the orientation with the apex of the curve pointed toward the tensioning element and the apex being pulled into the hole in the GVC/LA wall where the bridging element is pulling it unless some mechanisms, for example any of those described herein, are instituted to prevent flipping from occurring. When flipped or inverted, the anchor structure tends to focus the tensioning forces applied by the bridging element on the GVC/LA wall at a single point, the point of puncture between the LA/GVC wall. This increases the likelihood of tearing the wall and possibly pulling the posterior anchor into the atrium and releasing the tension altogether, or pulling partway into the atrium and relieving the tension to the point that the therapy is severely compromised.

This flipping movement described above would also be considerably less effective in pulling the wall of the LA toward the septum to affect reshaping of the annulus, thus would be less effective in providing therapy. With only a single point of contact between the curved posterior anchor and the GVC inner wall, the posterior anchor would be more likely to slide longitudinally within the GVC, whereupon the suture forming the bridging element would be more likely to slice the tissue forming the GVC/LA wall and expand the puncture hole, making it even more likely that the posterior anchor might get pulled through into the LA. Therefore, anti-flipping configurations and features can simultaneously provide an anti-sliding mechanism which would be doubly advantageous.

Figure 7A:
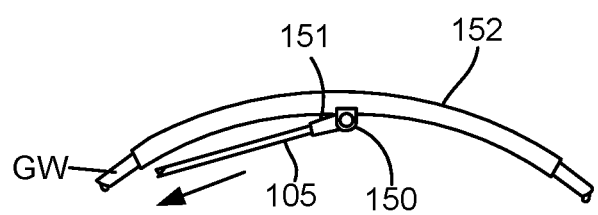
FIGS. 7A-7B illustrate a posterior anchor attached to a tensioning member with an anti-flipping feature, in accordance with some embodiments.
Figure 7B:
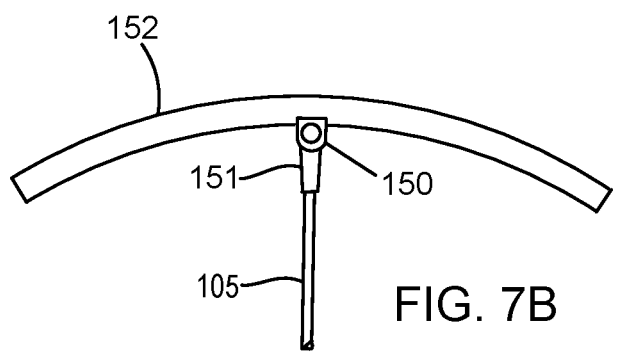

One such anti-flipping anchor configuration is shown in FIGS. 7A-7B. This anchor employs a rigid short link 151 that is attached by a hinge 150 or similar flexible attachment mechanism extending from the inside curve of anchor body 152. Link 151 is a relatively rigid length that can rotate to lay nearly flat against the inside curve of the curved anchor body 152 during delivery via a guidewire GW, as shown in FIG. 7A, and opens to be generally perpendicular to the anchor, as shown in FIG. 7B, when deployed by pulling the bridging element through a penetration in the wall of the LA. Typically, in the deployed configuration, the distal end of link 151 protrudes slightly into the LA in its resting position. In some embodiments, the link 151 is hollow such that the flexible bridging element 105 is attached to the curved posterior anchor body 152 through the hollow link 151. In other embodiments, the bridging element 105 is attached to the end extended away from anchor body 152. Link 151 is of sufficient length to cause coaxial alignment with tensioned bridging element 105 and prevent anchor from flipping over. Link 151 can be formed of a material such as plastic or smooth metal, and have a sufficient diameter that is less likely than the bare bridging element, for example a suture, to cut the tissue of the wall of the GVC where the penetration is made between the atrium and the GV. The link thus serves the double purpose of preventing flipping and protecting the wall of the GVC. The link is set to fold flat, pointing towards the puncture site during delivery and opening perpendicularly as the suture is tensioned at that site.

Figure 8:
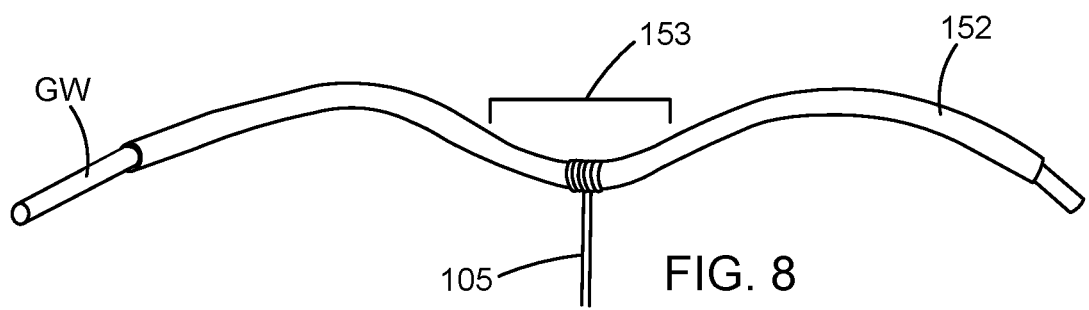
FIG. 8 illustrates a posterior anchor attached to a tensioning member with another anti-flipping feature, in accordance with some embodiments.

FIG. 8 illustrates another anchor embodiment, which includes an anti-flipping or anti-flipping feature defined as an inwardly curved portion 153 along where bridging element 105 attaches to the anchor body 152. When used within a left atrium implant for treatment of MVR, the inwardly curved mid-section projects into the plane of the generally GCV shaped curved anchor with the bridge 105 attached at the midsection of the anti-flipping curved portion 153. This allows for a simpler attachment to the anchor avoiding the complications of a linking mechanism both in its construction and delivery.

In another aspect, the posterior anchor can be configured with a delivery configuration and deployed configuration in which the anchor is eccentrically disposed along one side of a vessel wall. Such configurations can include structures and materials that are expandable as well as compressible so as to form an eccentric shape, which is non-circular and having a greater surface area on one side, which is to be engaged against a wall of the body lumen or vessel. Examples of such configuration are illustrated in the following embodiments.

Figure 9A:
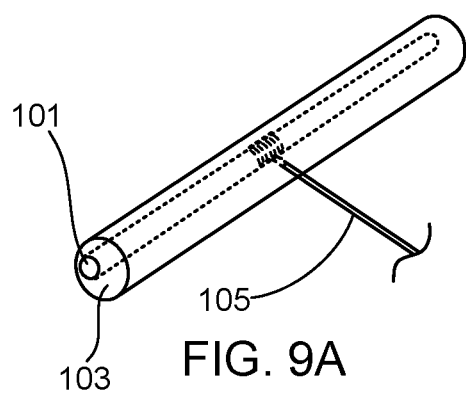
FIG. 9A illustrates a posterior anchor that includes a support element disposed in a far side of a compressible cylinder so as to deform the cylinder when tensioned, in accordance with some embodiments.
Figure 9B:
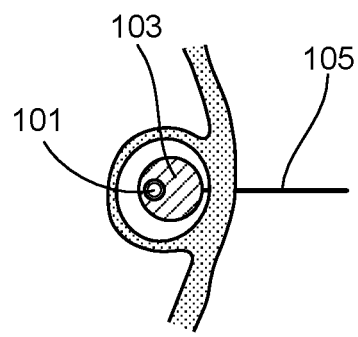
FIGS. 9B-9C illustrate the posterior anchor in FIG. 9A disposed within the GCV before and after deformation, respectively, in accordance with some embodiments.
Figure 9C:
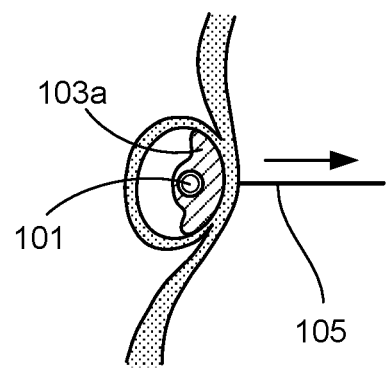

FIGS. 9A-9C illustrate a posterior anchor defined as crushable cylinder 103 with a more rigid support member 101, such as a T-bar support, attached or embedded within the cylinder. While a cylinder is described in this embodiment, it is appreciated that such an anchor could be configured in various elongate shapes including but not limited to partial cylinder, a crescent, an ovoid or various irregular shapes. Crushable cylinder can be formed of any suitable crushable material, such as a foam material or structure. Typically, rigid support member 101 is attached or embedded in the outer posterior diameter furthest from where the bridging element 105 extends, such as shown in FIG. 9A, so as to facilitate further crushing of the cylinder when the bridging element is tensioned. The rigid support member 101 can be substantially straight, as shown, or can be curved to generally follow the curve of the interior wall of the GVC and thus spread the pulling forces uniformly against the tissue wall.

FIGS. 9B-9C illustrate cross-sections of the posterior anchor of FIG. 9A disposed in the GVC before and after deployment, respectively. When delivered into the GVC, and connected to the bridging element 105, the crushable cylinder 103 is adjacent the wall of the GVC and LA, through which the bridging element 105 extends and the rigid support element 101 is disposed on the side furthest from the LA, as shown in FIG. 9B. Upon application of tension on the bridging element to the T-bar 101, the crushable material is collapsed into an eccentric shape 103a that has a reduced cross-section which is less obstructive of blood flow within the GVC. The crushed cylinder also assumes a shape which both more closely adheres to the inner shape of the GVC, thereby increasing the contact surface area as compared to the uncrushed cylinder. When crushed, the materials also somewhat compacted and generally stiffer than the uncrushed material which also helps spreads the forces applied by the bridging element over the surface area of the GVC wall.

It is appreciated that although the embodiment shown in FIGS. 9A-9C are shown as a relatively short elongated crushable member and T-bar, the T-bar or spine may be significantly longer to spread the pulling force and may be shaped with a curve to spread the force more generally in the curved shaped GVC.

In some embodiments, the crushable materially is a material that encourages tissue ingrowth and or scarring to create a tissue-anchor matrix. This ingrowth further aids in assuring that the posterior anchor is not pulled through the GVC wall or flipped within the GVC. This crushable material may be constrained by the delivery catheter in a crushed form to lower its delivery profile thus aiding delivery, and when released is further reshaped to its final dimension by the bridging element.

Figure 10A:
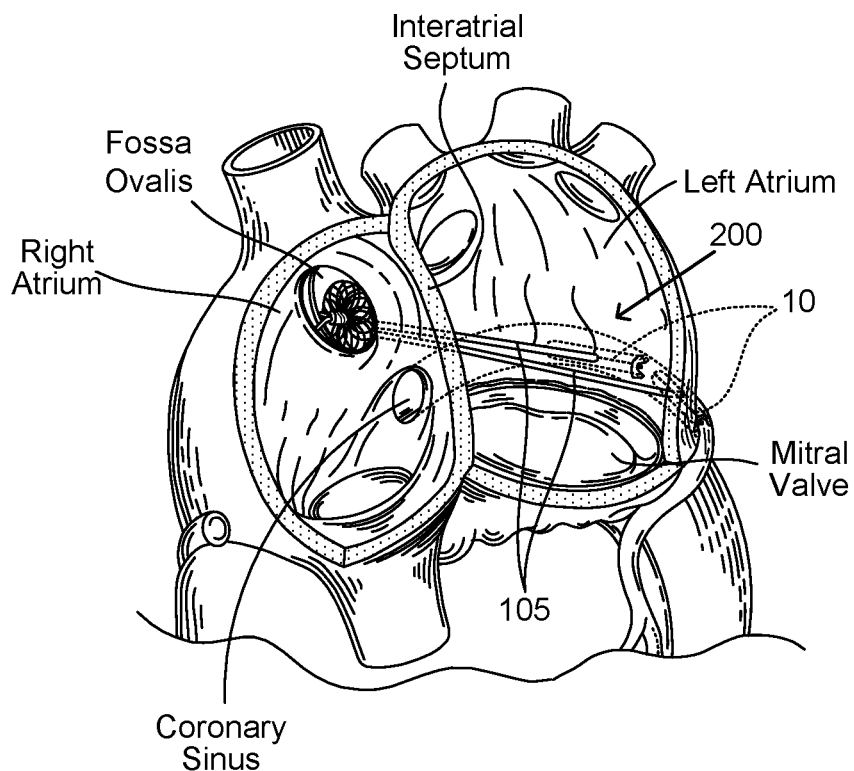
FIG. 10A illustrates a heart implant system having an anterior anchor and multiple bridge elements, each extending to a separate posterior anchor within the GCV, in accordance with some embodiments.
Figure 10B:
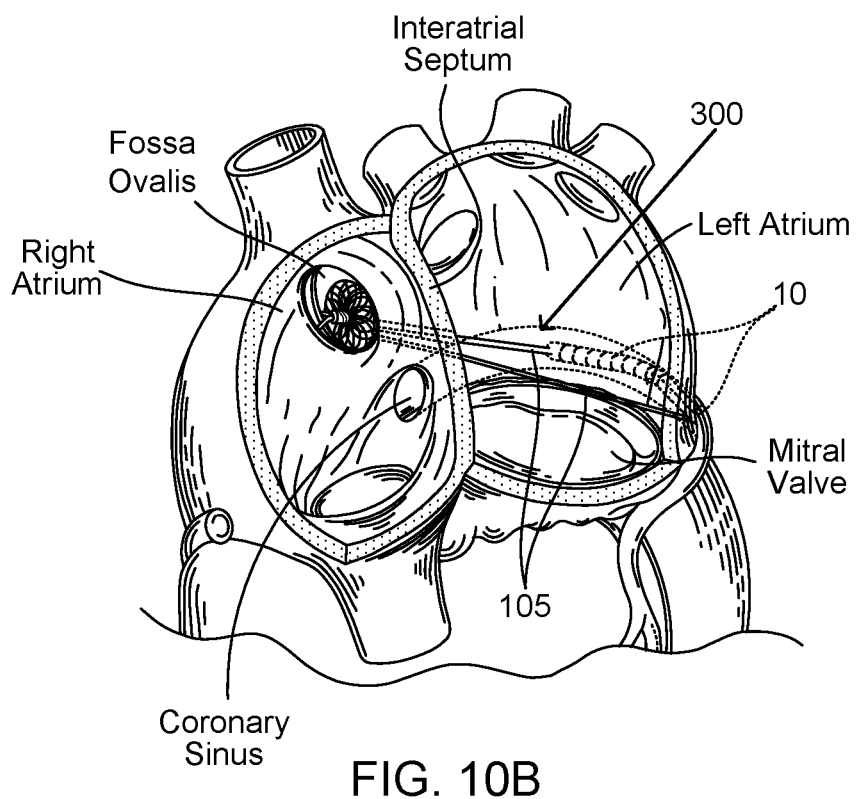
FIG. 10B illustrates a heart implant system having an anterior anchor and multiple bridge elements extending to a single posterior anchor within the GCV, in accordance with some embodiments.
Figure 10C:
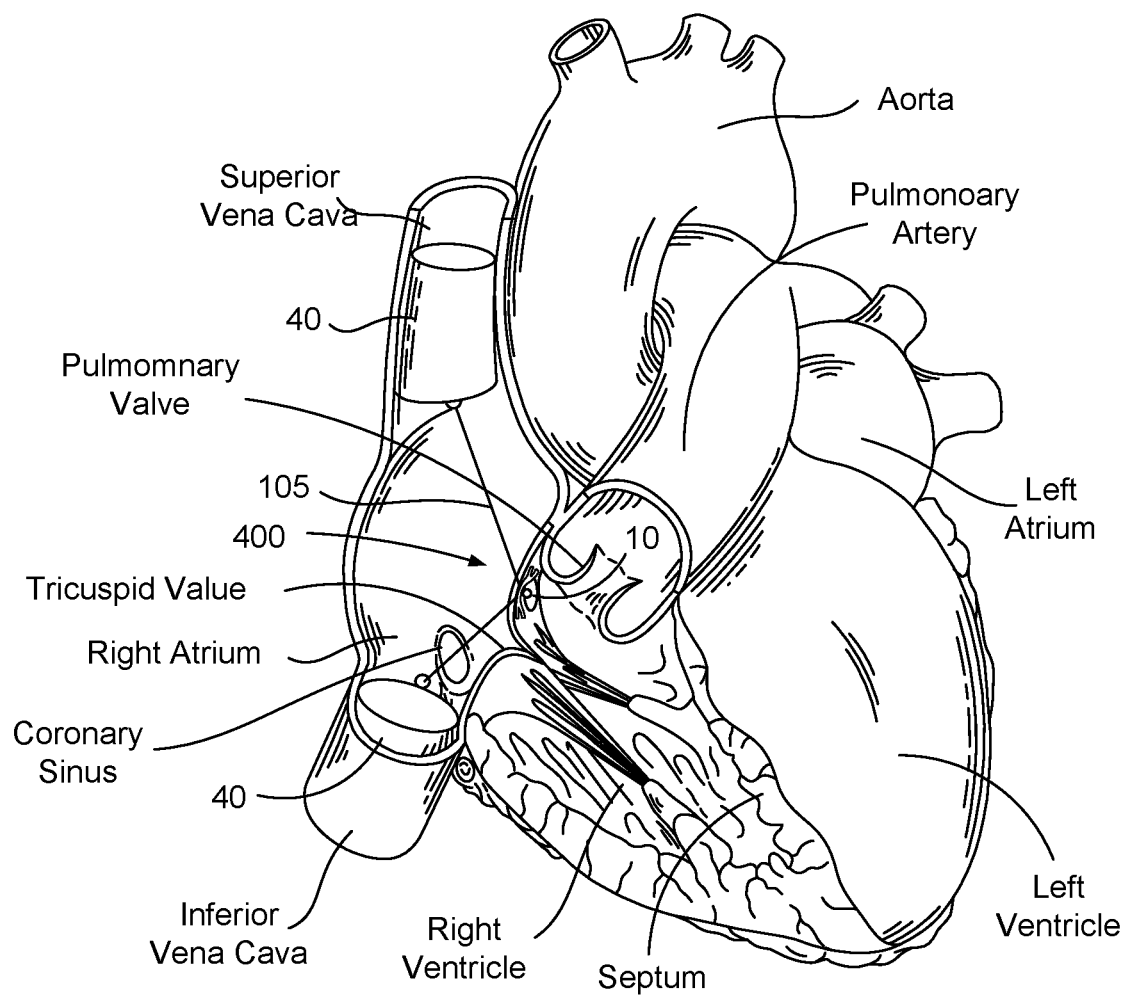
FIG. 10C illustrates a heart implant system for reshaping the tricuspid valve, the system having two bridge elements extending from anchors in the superior and inferior vena cava to a posterior anchor disposed in the right ventricle, in accordance with some embodiments.

FIGS. 10A-10B illustrate alternative implant systems that can utilize posterior anchors in accordance with those described herein. FIG. 10A illustrates a heart implant system 200 having an anterior anchor and multiple bridge elements 105 extending to multiple posterior anchors 10 within the GCV. In this embodiment, the posterior anchor 10 is a collapsible cylindrical structure, such as that described in FIG. 13A. FIG. 10B illustrates a heart implant system 300 having an anterior anchor and multiple bridge elements 105 extending to a single posterior anchor 10 deployed within the GCV. In this embodiment, posterior anchor 10 is a segmented tube, such as that described in FIG. 11G. It is appreciated that each of the posterior anchors depicted can utilize any one or combination of the anchor features in any of the embodiments described herein. FIG. 10C illustrates a heart implant system 400 for reshaping the tricuspid valve, the system having two bridge elements extending from anchors 40 in the superior and inferior vena cava to a posterior anchor 10 disposed in the right ventricle, in accordance with some embodiments. In this embodiment, the posterior anchor 10 is a collapsible cylindrical structure, such as that described in FIG. 13A.

In another aspect, curved posterior anchors are provided that can be transformed from a substantially linear configuration to a curvilinear configuration. In some embodiments, the curve of the anchor can be adjusted during deployment. Some such posterior anchors include a series of interfacing or interconnecting components that articulate into a curved shape when tensioned, either by the bridging element or by one or more tethers extending therethrough. These anchors can be configured for use with systems having a single bridging element per anchor, such as that shown in FIG. 10A, or in systems having multiple bridging elements, such as that shown in FIG. 10B. In some embodiments, the curveable posterior anchor is defined within a single tube having a series of cuts or kerfs that allow for controlled articulation or curvature of the anchor body by the tensioned bridge. Adjustment of such anchors can include multiple schemes and anchor configurations. Examples of such configurations are detailed further below.

FIGS. 11A-11D illustrate a posterior anchor configured that curves inwardly toward the bridging element when deployed. Such as configuration can be designed to match a curvature of a vessel or an adjacent tissue or organ wall, and further resists flipping since the curvature can be maintained by the tensioned bridge element. Typically, the posterior anchor is defined so as to match the curvature of the GVC to more evenly and securely spread the anchor forces provided by the attachment through the bridging element which is tensioned against the anterior anchor.

Figure 11A:
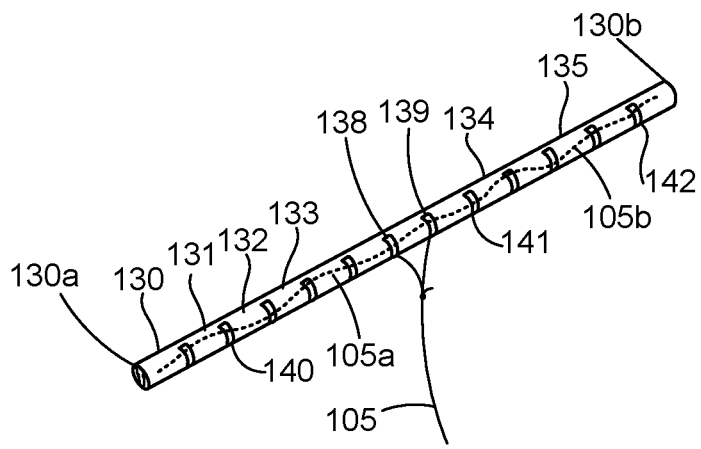
FIGS. 11A-11G illustrate posterior anchors that are curvable or conformable upon adjustment of the tensioning member by use of one or more tethers, in accordance with some embodiments.
Figure 11B:
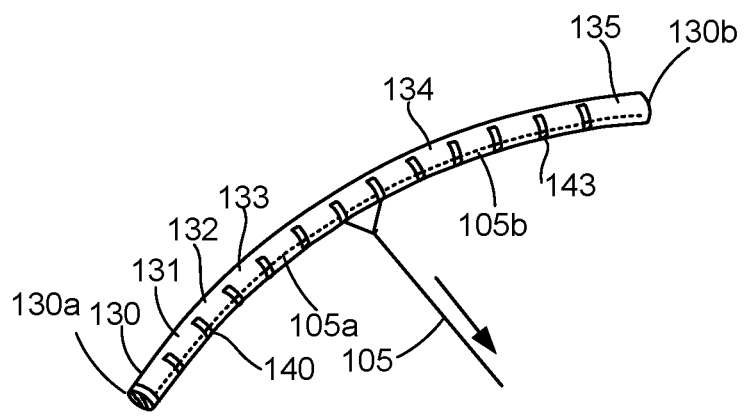

The embodiments of FIG. 11A-11D can be a segment tube formed from a single tube. One way this can be accomplished is to cut a hollow metal or polymeric tube 130 of a suitable length (e.g. a length that matches the mitral annulus along the GVC) into a series of segments 131,132,133 by a series of cuts called kerfs 140,141,142, as shown in FIG. 11A. The kerfs can be a depth for example, of ½ to ¾ of the diameter of the tube, and can also be angled to facilitate tighter radius of curvature. These areas are open, meaning that some material is cut out of the tube to define a series of segments, which allows the tube to preferentially bend in the direction of the kerfs when force is applied to both ends 130a, 130b.

One or more tethers can be used to draw segments inward to curve the anchor. In some embodiments, the internal tethers 105a, 105b are each fixed internally at the respective ends 130a, 130b of the tube and allowed to exit along a center portion of the anchor through one of the kerfs or perhaps two of the kerfs 138,139 (for example, as in FIGS. 11A-11B), and a bridging element is attached to the exposed tethers. Tensioning the bridging element against the GCV wall simultaneously shortens the minor axis of the mitral valve and bends the anchor to the desired shape. Such a configuration causes tube 130 to curve when the bridging element 105 is tensioned. The more tension applied, the greater the curvature toward the bridging element, until the kerf openings are closed or the engaged tissue exerts an equal countering force on the tubular body 130. This is particularly advantageous for use in a dynamic environment, such as the heart, since the aforementioned flipping typically occur when the bridging element experiences heightened tension.

Figure 11C:
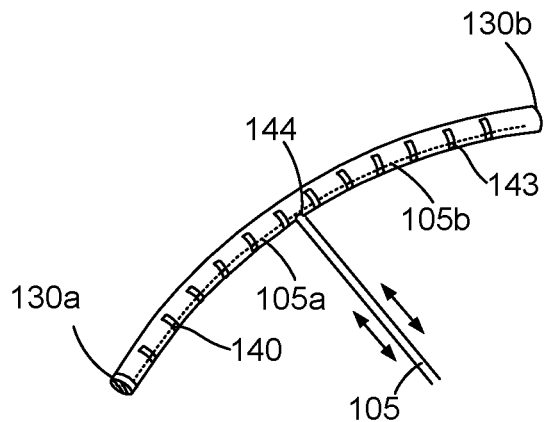

FIG. 11C illustrates a similar embodiment having internal tethers 105a, 105b that are coupled with ends 130a, 130b and that exit through a central opening 144 and couple with the bridging element 105. Alternatively, tethers 105a, 105b can be each independently fixed to ends 130a, 130b and exit from the center of the anchor so as to allow for independent bending of each end. This approach can provide a configuration that provides for multiple segments and custom shaped anchor.

Figure 11D:
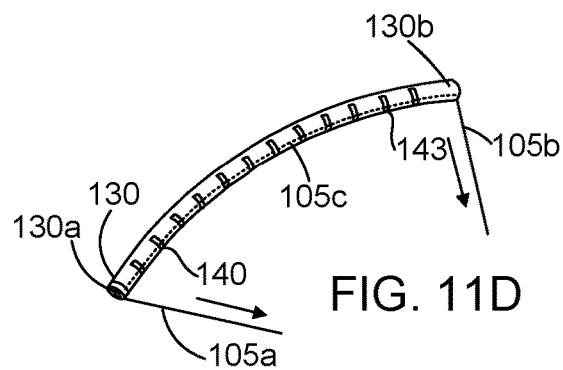

FIG. 11D illustrates an alternative embodiment in which the bridging element 105 is a loop that extends through the tubular body 130 of the anchor such that, when tensioned by shortening the loop, the internal tether portion 105c shortens and tensioned tether portions 105a, 105b force ends 130a, 130b inward, thereby curving the anchor body. The length of the loop can be shortened by pulling one or more free ends of the loop through and attaching to the anterior anchor, thereby allowing the user to adjust the tension of the bridging elements.

Alternatively, the bending may be independent of the bridging element. FIG. 11E illustrates an example of such a bending scheme using a catheter in the GCV to pull on an internal tether 106 fixed internally to the distal end of the anchor though a lumen of the catheter. This causes the anchor's proximal end to engage the catheter tip and bend. A fastener 107, such as a clip, knot or any suitable mechanism, can be used to fix the bent anchor in the desired curved position and the excess tether is cut free.

It is appreciated that the bent configuration and the force required to bend the tube, as well as the stiffness of the bent tube can be varied as desired by adjusting the number, width, spacing and depth of the kerfs. The kerfs may be of varied length along the anchors length, combining wider and narrower sections to relatively stiffen or soften sections respectively. The curving of anchor may be achieved a single shared connected bridge or dual independent bridge elements with the latter allowing for more relaxed curve one end.

In another similar approach, the anchor is defined by individual unconnected hollow links that are similar or tailored in length. The links are formed so as to have a desired stiffness and shape for their resting location when deployed. The links can be formed using any of the constructions detailed herein. Such embodiments can utilize a delivery scheme having a single bridge with a first bridge end deployment followed by loading of the anchor or anchor links to their resting location followed by deployment of the second bridge. The tips of the anchor or outer links may have grommets or other means of protecting tissue from any abrasion from the bridging element.

In another aspect, a hybrid concept of a bendable GVC anchor with two end bridges is provided. An example of such an embodiment can include a bendable anchor resembling a string of segments or interfacing elements that extends between bridge elements and attached at each end. In some embodiments, the bridging elements are permanently fixed to each end of the anchor. The first bridge is preferably deployed farthest from the coronary sinus followed by the second with a spacing between the punctures equal to length of the anchor, which would preferably be centered over the larger central scallop leaflet of the mitral valve. The anchor is then deployed by pulling both bridges and the anchor through a protective sheath. In some embodiments, the ends of the individual segments are angled so that when the entire string is pulled tight and the ends abut, the length of the string of segments forms a curved structure. The curved structure can be preselected dependent on the angles of the segments, and need not be a constant curve. For example, such an anchor could include a relatively straight section at the center of the anchor and a more sharply curved section at each end. Alternatively, an anchor could include a straight segment and an even more sharply curved segment on the other end of the anchor, which may be a useful configuration in some applications.

Figure 11F:
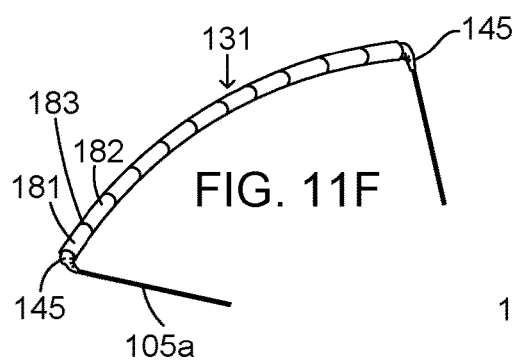
Figure 11G:
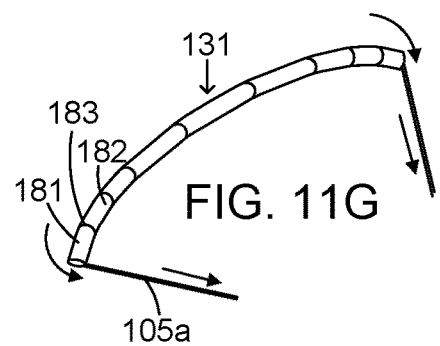
Figure 11E:
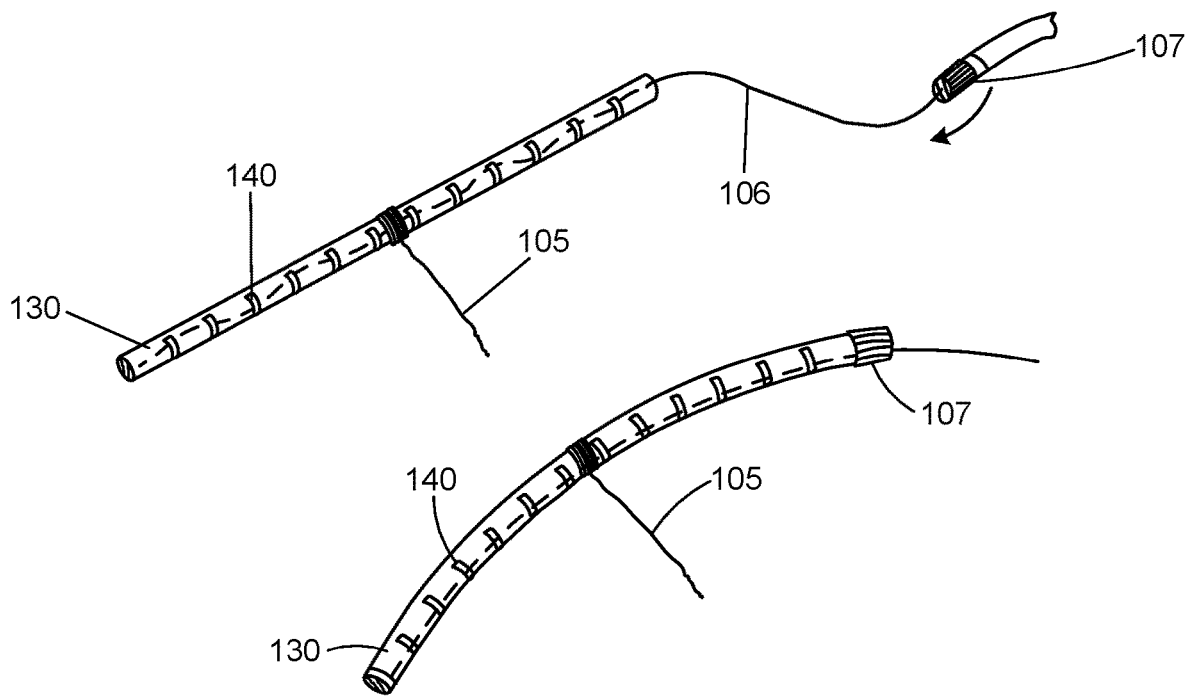

FIGS. 11F and 11G illustrate examples of the above described alternative approach for achieving a curved posterior anchor by use of individual links. The links can be unconnected with interfacing surfaces between each, or can be interconnected in a manner that allows relative movement between adjacent links to allow for curvature of the anchor. In these depicted embodiments, tube 131 is formed by a number of individual segments 181, 182, which can be shaped with mating surfaces 183 that are either straight or angled as desired. In the embodiment of FIG. 11F, the end of the anchor tube may be protected by grommets 145 connected to bridging elements 105a, 105b. In some embodiments, the grommets 145 are configured as fixed stops fixing a bridging element or tether extending therethrough to a preset length so as to provide a pre-determined curvature to the anchor. In the embodiment of FIG. 11G, the links of the anchor are laced over a single bridging element or tether and are free to move along the bridge such that shortening of the bridging element or tether engages opposite ends of the anchor so as to curve the anchor. Such a configuration allows links to be added or configured to vary length or stiffness along the anchor. In either embodiment, the two bridging elements 105a, 105b may be attached to the same location on the anterior anchor. Applying tension to those bridging elements curves tube 131 inward. When such an anchor is incorporated into a heart implant system, the curved tube 131 pulls the entire wall of the LA toward the septum and advantageously shapes the mitral valve annulus with the operator able to bias the length towards toward one side or the other while viewing the regurgitant flow on ultrasound in real time. Although the links or segments are shown here as hollow tubular segments, it is appreciated that the links could be formed in various sizes and shapes, including shapes contoured to match a curvature of a vessel or the patient's anatomy. In some embodiments, the links are defined as a string of interfacing element such that shortening of the bridging element or tether articulates the links into a curved arrangement along the anchor. The interfacing elements can be of any suitable construction (e.g. solid, hollow) and can be of formed in any shape desired.

Similar to these examples, in that the configurations requires multiple bridging element attachment to the anterior anchor, would be a sequence of posterior anchors each separately attached, such as shown in FIG. 10A. Such a configuration would make possible separate individual attachments that could apply tension at various angles to optimally deform the LA wall and mitral valve annulus to reduce mitral regurgitation. Each posterior anchor could employ the shapes and features of any of the posterior anchors described above. Each could attach to the same location on the anterior anchor, or could attach at slightly different locations in the anterior anchor or even separate anterior anchors to optimize the angles of tension for maximum effect.

In another aspect, the posterior anchor can include an expandable structure that can be collapsed so as to engage at least a portion of one side of the vessel in which it is deployed as well as to assume a reduced profile to allow improve blood flow therethrough. Example of such embodiments include a scaffold or wire form structure configured to be expanded within the vessel after delivery, then collapsed laterally by tensioning of the bridging element. Such embodiments can include a wire form structure having weakened portions extending longitudinally on opposite sides of the wire form structure to facilitate lateral collapse. The structures can be self-expanding or balloon deployable. In some embodiments, the collapsible wire form structure include one or more support ribs extending longitudinally to reinforce the collapsed structure to improve anchoring and adherence of the structure along a length of the body vessel. Such reinforcing ribs can be straight or can be curved as needed for a particular anatomy.

FIGS. 12A-12C and 13A-13B illustrate examples of the above described collapsible wire form cylinder structure 120. Typically, the wire form structure is a cylinder mesh structure that may be delivered in low profile and expand to the desired diameter, either by self-expansion or balloon expansion. The cylinder mesh structure can include a posterior backbone 122 that forms a T-bar and attaches to the bridging element 105.

Figure 12A:
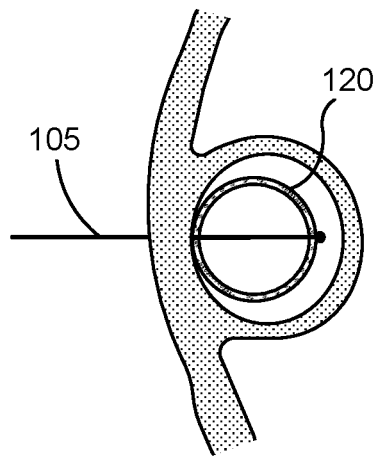
FIGS. 12A-12C illustrate posterior anchors defined by expandable structures that are laterally collapsible upon tensioning of a support backbone, in accordance with some embodiments.
Figure 12B:
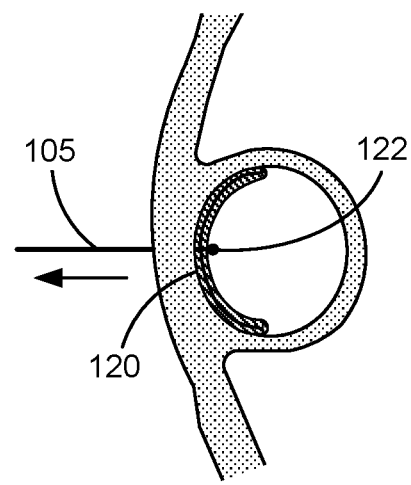
Figure 12C:
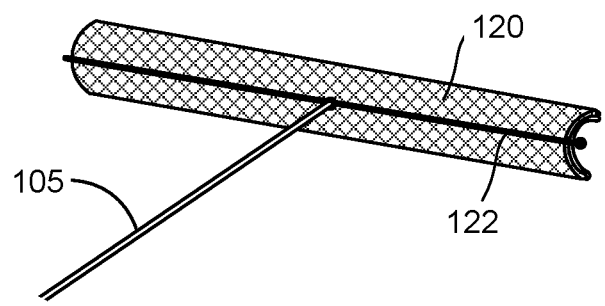

As shown in FIG. 12A, after deployment of the cylinder mesh structure 120 in a vessel, such as the GCV, the bridge element 105 extends to the support backbone 122 disposed on the opposing side of the cylindrical mesh structure 120 from where bridge element 105 extends through the wall of the GCV/LA. When tension is applied by the bridging element 105 to the backbone, the support crushes the cylinder mesh structure wall upon itself creating a flattened ribbon against the LA/GCV wall. Such a configuration is advantageous as it forms a stiff, relatively flat surface that effectively spreads the force of the tensioning against the wall to prevent the posterior anchor from being pulled through the GVC wall. Further, the folded design doubles the wall thickness and thus its strength and increases its purchase of the GCV wall up to 1.5 times its uncrushed diameter. Such a configuration allows for improved ease of deployment and allows the anchor to be embedded in the wall of the GVC upon deployment. Furthermore, the mesh structure of the scaffold further promotes tissue ingrowth.

Figure 13A:
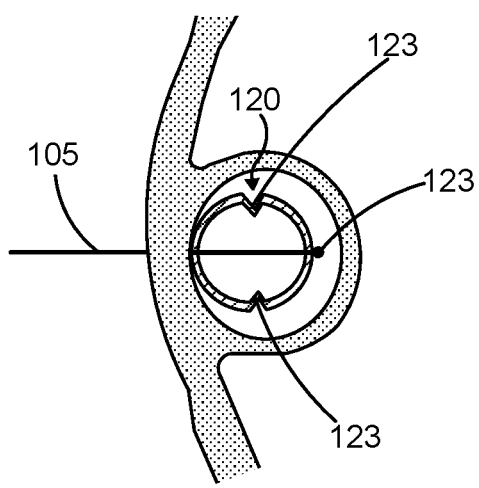
FIGS. 13A-13B illustrate an alternative posterior anchors defined by expandable structures having folding zones that facilitate lateral collapse upon tensioning of a support backbone, in accordance with some embodiments.
Figure 13B:
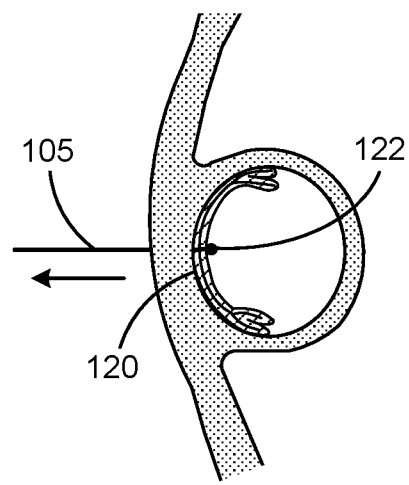

FIGS. 13A-13B illustrate another embodiment of a collapsible scaffold structure 120 that includes folding zones or softer sections 123 to insure preferential folding along predetermined lines. These folding zones extend longitudinally along most or all of the length of the cylindrical structure and can be defined by scores, weakened portions, or previous deformation to facilitate folding of the cylindrical mesh structure along these areas when deployed. Also, as with the crushable foam embodiment, the material or coating of the wire form structure, and the surface structure of the crushable wire form structure might be such that it spurs the ingrowth of tissue to, over time, form a tissue-anchor matrix. In either embodiment, the support backbone can be substantially straight, or preferably, curved to generally mimic the curve of the interior wall of the GVC. The scaffold can be a mesh structure, which can be defined to promote tissue-ingrowth.

The foregoing is considered as illustrative only of the principles of the invention. The embodiments herein disclosed merely exemplify the invention which may be embodied in other specific structures. While preferred embodiments have been described, the details may be changed without departing from the invention. Further, most of the inventions are shown in simple forms to illustrate elemental function and features and may be combined to a final embodiment that uses one more elements combined into a single device. It is also anticipated that the embodiments described may be combined, by way of example but not by way of limitation, having a curbed backbone in the crushable foam, or multiple curved anchors with anti-flipping features or configurations with multiple attachments to the anterior anchor. Furthermore, since numerous modifications and changes will readily occur to those skilled in the art, the invention is not limited to the construction and operation shown and described in the preferred embodiments except as limited by the claims.

What is claimed is:

1. A method of anchoring an implant and reshaping a body organ of a patient, the method comprising:
    delivering and deploying an anterior anchor within a desired location along or within an organ of a patient;
    delivering a posterior anchor within a vasculature of the patient adjacent the body organ, the posterior anchor being conformable to an anatomy of the patient upon deployment of the posterior anchor, wherein the posterior anchor is a cylindrical body that is laterally deformable or collapsible and has a substantially rigid backbone attached to the cylindrical body;
    delivering a first bridging element that extends across a chamber of the organ between the anterior anchor and the posterior anchor so as to attach the anterior anchor with the posterior anchor with the first bridging element penetrating through a tissue against which the posterior anchor is engaged when the implant is deployed; and
    conforming the posterior anchor to a desired shape to accommodate the anatomy of the patient by tensioning the first bridging element while interfaced with the posterior anchor and the anterior anchor, wherein tensioning the first bridging element comprises shortening the first bridging element to maintain a desired spacing between the anterior anchor and the posterior anchor so as to reshape the body organ by engagement of the conformed posterior anchor, wherein conforming the posterior anchor comprises tensioning the first bridging element while attached to the substantially rigid backbone so as to deform or collapse the cylindrical body.

2. The method of claim 1, wherein the cylindrical body is a compressible foam material and the substantially rigid backbone is disposed within or on the cylindrical body.

3. The method of claim 1, wherein the cylindrical body is an expandable scaffold that includes folding zones extending longitudinally and offset from the substantially rigid backbone,
    wherein conforming the posterior anchor comprises laterally collapsing the scaffold by folding the scaffold along the folding zones while tensioning the bridging element attached to the substantially rigid backbone.

4. The method of claim 1, wherein the cylinder is an expandable scaffold, the method further comprising:
    delivering the scaffold in a radially compressed configuration via a guidewire or catheter; and
    radially expanding the scaffold within the vasculature before laterally collapsing the scaffold.

5. The method of claim 1, wherein the posterior anchor comprises a segmented tube having a plurality of segments and the first bridging element comprises a first tether attached to a first end of the segmented tube and exits the segmented tube along a central portion thereof;

wherein shortening the first bridging element comprises shortening the first tether thereby curving a portion of the segmented tube between the first end and the central portion.

6. The method of claim 5, further comprising:

wherein conforming the posterior anchor comprises shortening a second tether extending from a second opposite side of the segmented tube and exiting the segmented tube along the central portion thereof thereby curving another portion of the segmented tube between the second end and the central portion.

7. The method of claim 5, wherein the bridging element extends directly between a first end of the segmented tube and the anterior anchor and a second opposite end of the segmented tube is attached to the anterior anchor by a second bridging element, the method further comprising:

wherein conforming the posterior anchor comprises shortening the second bridging element so as to place the second bridging element under tension, wherein tensioning the first and second bridging elements under tension curves the segmented tube so as to conform to anatomy against which the posterior anchor is engaged.

8. The method of claim 5, wherein the posterior anchor comprises a segmented tube having a plurality of segments, wherein the first bridging element comprises a tether passed longitudinally through the segmented tube and exiting at or near opposite ends of the segmented tube, wherein shortening the bridge portion comprises shortening the tether thereby drawing opposite ends of the segment tube inward so as to curve the posterior anchor.

9. The method of claim 1, wherein the posterior anchor comprises a string of interfacing elements with one or more tethers extending through the interfacing elements and attach and attached to the first bridging element, the interfacing elements being formed of any suitable material and shape, wherein shortening the first bridging element comprises shortening the one or more tethers thereby curving at least a portion of the string of interfacing elements.

10. The method of claim 1, wherein the entire implant is delivered and deployed intravascularly.

\* \* \* \* \*